(12) United States Patent
Rogers et al.

(10) Patent No.: US 9,861,399 B2
(45) Date of Patent: Jan. 9, 2018

(54) INTERSPINOUS PROCESS IMPLANT HAVING A BODY WITH A REMOVABLE END PORTION

(71) Applicant: Spinal Simplicity, LLC, Overland Park, KS (US)

(72) Inventors: Adam Rogers, Suffolk, VA (US); Melissa Frock, Larwill, IN (US); Todd Moseley, Olathe, KS (US); Harold Hess, Leawood, KS (US); Jeff Slover, Lee's Summit, MO (US); Adam Frock, Larwill, IN (US); Douglas Snell, Overland Park, KS (US)

(73) Assignee: Spinal Simplicity, LLC, Overland Park, KS (US)

( * ) Notice: Subject to any disclaimer, the term of this patent is extended or adjusted under 35 U.S.C. 154(b) by 0 days.

(21) Appl. No.: 15/159,189

(22) Filed: May 19, 2016

(65) Prior Publication Data

US 2016/0262805 A1 Sep. 15, 2016

Related U.S. Application Data

(63) Continuation-in-part of application No. 13/940,868, filed on Jul. 12, 2013, now Pat. No. 9,757,164, and a
(Continued)

(51) Int. Cl.
*A61B 17/70* (2006.01)
*A61B 17/00* (2006.01)

(52) U.S. Cl.
CPC .... *A61B 17/7068* (2013.01); *A61B 17/00234* (2013.01); *A61B 17/7065* (2013.01); *A61B 2017/00004* (2013.01)

(58) Field of Classification Search
CPC .............. A61F 2/4611; A61B 17/7065; A61B 17/7067; A61B 17/7068; A61B 17/7071
See application file for complete search history.

(56) References Cited

U.S. PATENT DOCUMENTS

| 1,346,578 A | 7/1920 | Windsor |
| 4,116,104 A | 9/1978 | Kennedy |

(Continued)

FOREIGN PATENT DOCUMENTS

| CN | 102137628 A | 7/2011 |
| GB | 2 436 292 A | 9/2007 |

(Continued)

OTHER PUBLICATIONS

US 7,520,878, 04/2009, Michelson (withdrawn)
(Continued)

*Primary Examiner* — Eduardo C Robert
*Assistant Examiner* — Michelle C Eckman
(74) *Attorney, Agent, or Firm* — Locke Lord LLP; Scott D. Wofsy; Arpita G. Buesing

(57) ABSTRACT

An interspinous process implant is disclosed that includes an elongated threaded implant body defining a longitudinal axis and having a main body portion with opposed proximal and distal end portions, and a removable body portion operatively connected to the proximal end portion of the main body portion, a distal anchor assembly including two deployable anchor blades mounted for pivotal movement between a stowed position located within an interior cavity of the main body portion and a deployed position radially extending from the main body portion, and a proximal anchor assembly including an anchor collar mounted for longitudinal movement along the longitudinal axis of the implant body between a first position spaced apart from the
(Continued)

distal anchor assembly and a second position approximated with the distal anchor assembly.

33 Claims, 30 Drawing Sheets

Related U.S. Application Data continuation-in-part of application No. 15/085,687, filed on Mar. 30, 2016, which is a continuation of application No. 14/560,006, filed on Dec. 4, 2014, now Pat. No. 9,314,276, which is a continuation of application No. 12/554,922, filed on Sep. 7, 2009, now Pat. No. 8,945,184.

(60) Provisional application No. 62/165,634, filed on May 22, 2015, provisional application No. 61/749,595, filed on Jan. 7, 2013, provisional application No. 61/209,997, filed on Mar. 13, 2009.

(56) References Cited

U.S. PATENT DOCUMENTS

| | | |
|---|---|---|
| 4,573,844 A | 3/1986 | Smith |
| 4,599,086 A | 7/1986 | Doty |
| 4,632,101 A | 12/1986 | Freedland |
| 4,721,103 A | 1/1988 | Freedland |
| 4,998,936 A | 3/1991 | Mehdian et al. |
| 5,098,433 A | 3/1992 | Freedland |
| 5,209,621 A | 5/1993 | Burbidge |
| 5,417,531 A | 5/1995 | Brown |
| 5,499,894 A | 3/1996 | Alto et al. |
| 5,514,180 A | 5/1996 | Heggeness et al. |
| 5,609,635 A | 3/1997 | Michelson |
| 5,645,599 A | 7/1997 | Samani |
| 5,653,761 A | 8/1997 | Pisharodi |
| 5,702,391 A | 12/1997 | Lin |
| 5,800,547 A | 9/1998 | Schafer et al. |
| 5,800,550 A | 9/1998 | Sertich |
| 5,836,948 A | 11/1998 | Zucherman et al. |
| 5,849,004 A | 12/1998 | Bramlet |
| 5,860,977 A | 1/1999 | Zucherman et al. |
| 5,876,404 A | 3/1999 | Zucherman et al. |
| 5,876,457 A | 3/1999 | Picha et al. |
| 5,894,004 A | 4/1999 | Wagner et al. |
| 5,904,686 A | 5/1999 | Zucherman et al. |
| 5,968,098 A | 10/1999 | Winslow |
| 6,017,342 A | 1/2000 | Rinner |
| 6,045,552 A | 4/2000 | Zucherman et al. |
| 6,048,342 A | 4/2000 | Zucherman et al. |
| 6,068,630 A | 5/2000 | Zucherman et al. |
| 6,074,390 A | 6/2000 | Zucherman et al. |
| 6,090,112 A | 7/2000 | Zucherman et al. |
| 6,093,207 A | 7/2000 | Pisharodi |
| 6,149,652 A | 11/2000 | Zucherman et al. |
| 6,152,926 A | 11/2000 | Zucherman et al. |
| 6,156,038 A | 12/2000 | Zucherman et al. |
| 6,174,334 B1 | 1/2001 | Suddaby |
| 6,183,471 B1 | 2/2001 | Zucherman et al. |
| 6,190,387 B1 | 2/2001 | Zucherman et al. |
| 6,203,260 B1 | 3/2001 | Henline et al. |
| 6,235,030 B1 | 5/2001 | Zucherman et al. |
| 6,238,397 B1 | 5/2001 | Zucherman et al. |
| 6,245,108 B1 | 6/2001 | Biscup |
| 6,257,803 B1 | 7/2001 | McCabe et al. |
| 6,264,677 B1 | 7/2001 | Simon et al. |
| 6,280,444 B1 | 8/2001 | Zucherman et al. |
| 6,332,882 B1 | 12/2001 | Zucherman et al. |
| 6,332,883 B1 | 12/2001 | Zucherman et al. |
| 6,379,355 B1 | 4/2002 | Zucherman et al. |
| 6,402,750 B1 | 6/2002 | Atkinson et al. |
| 6,419,676 B1 | 7/2002 | Zucherman et al. |
| 6,419,677 B2 | 7/2002 | Zucherman et al. |
| 6,451,019 B1 | 9/2002 | Zucherman et al. |
| 6,451,020 B1 | 9/2002 | Zucherman et al. |
| 6,478,796 B2 | 11/2002 | Zucherman et al. |
| 6,500,178 B2 | 12/2002 | Zucherman et al. |
| 6,514,256 B2 | 2/2003 | Zucherman et al. |
| 6,610,092 B2 | 8/2003 | Ralph et al. |
| 6,626,944 B1 | 9/2003 | Taylor |
| 6,652,527 B2 | 11/2003 | Zucherman et al. |
| 6,652,534 B2 | 11/2003 | Zucherman et al. |
| 6,682,564 B1 | 1/2004 | Duarte |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,709,435 B2 | 3/2004 | Lin |
| 6,712,819 B2 | 3/2004 | Zucherman et al. |
| 6,733,534 B2 | 5/2004 | Sherman |
| 6,743,256 B2 | 6/2004 | Mason |
| 6,746,485 B1 | 6/2004 | Zucherman et al. |
| 6,761,720 B1 | 7/2004 | Senegas |
| 6,770,096 B2 | 8/2004 | Bolger et al. |
| 6,783,546 B2 | 8/2004 | Zucherman et al. |
| 6,796,983 B1 | 9/2004 | Zucherman et al. |
| 6,849,093 B2 | 2/2005 | Michelson |
| 6,860,977 B2 | 3/2005 | Heinz et al. |
| 6,884,012 B2 | 4/2005 | Panasik |
| 6,902,566 B2 | 6/2005 | Zucherman et al. |
| 6,926,728 B2 | 8/2005 | Zucherman et al. |
| 6,946,000 B2 | 9/2005 | Senegas et al. |
| 6,949,123 B2 | 9/2005 | Reiley |
| 7,001,126 B2 | 2/2006 | Lesecq |
| 7,029,473 B2 | 4/2006 | Zucherman et al. |
| 7,041,135 B2 | 5/2006 | Michelson |
| 7,083,649 B2 | 8/2006 | Zucherman et al. |
| 7,101,375 B2 | 9/2006 | Zucherman et al. |
| 7,125,425 B2 | 10/2006 | Foley et al. |
| 7,189,234 B2 | 3/2007 | Zucherman et al. |
| 7,192,446 B2 | 3/2007 | Shapiro et al. |
| 7,201,751 B2 | 4/2007 | Zucherman et al. |
| 7,217,291 B2 | 5/2007 | Zucherman et al. |
| 7,226,261 B1 | 6/2007 | Bristol |
| 7,232,464 B2 | 6/2007 | Mathieu et al. |
| 7,238,186 B2 | 7/2007 | Zdeblick et al. |
| 7,238,204 B2 | 7/2007 | Le Couedic et al. |
| 7,241,094 B1 | 7/2007 | Potts et al. |
| 7,306,628 B2 | 12/2007 | Zucherman et al. |
| 7,320,707 B2 | 1/2008 | Zucherman et al. |
| 7,326,248 B2 | 2/2008 | Michelson |
| 7,410,501 B2 | 8/2008 | Michelson |
| 7,423,268 B2 | 9/2008 | Ren |
| 7,445,636 B2 | 11/2008 | Michelson |
| 7,445,637 B2 | 11/2008 | Taylor |
| 7,465,317 B2 | 12/2008 | Malberg et al. |
| 7,465,318 B2 | 12/2008 | Sennett et al. |
| 7,476,251 B2 | 1/2009 | Zucherman et al. |
| 7,481,839 B2 | 1/2009 | Zucherman et al. |
| 7,481,840 B2 | 1/2009 | Zucherman et al. |
| 7,497,859 B2 | 3/2009 | Zucherman et al. |
| 7,503,935 B2 | 3/2009 | Zucherman et al. |
| 7,510,567 B2 | 3/2009 | Zucherman et al. |
| 7,520,899 B2 | 4/2009 | Zucherman et al. |
| 7,662,187 B2 | 2/2010 | Zucherman et al. |
| 7,824,429 B2 | 11/2010 | Culbert et al. |
| 7,918,875 B2 | 4/2011 | Lins et al. |
| 8,007,517 B2 | 8/2011 | Lins et al. |
| 8,132,435 B2 | 3/2012 | Thomas et al. |
| 8,157,840 B2 | 4/2012 | Zucherman et al. |
| 8,343,190 B1 | 1/2013 | Mueller et al. |
| 8,403,959 B2 | 3/2013 | Dollinger |
| D692,562 S | 10/2013 | Hess |
| 8,702,757 B2 | 4/2014 | Thommen et al. |
| 8,858,598 B2 | 10/2014 | Seifert et al. |
| 8,945,184 B2 | 2/2015 | Hess et al. |
| 9,314,276 B2 | 4/2016 | Hess et al. |
| 2001/0046429 A1 | 11/2001 | Gaudron |
| 2002/0015629 A1 | 2/2002 | Ito |
| 2002/0100244 A1 | 8/2002 | Carroll |
| 2004/0024463 A1 | 2/2004 | Thomas et al. |
| 2004/0127906 A1 | 7/2004 | Culbert et al. |
| 2004/0193158 A1 | 9/2004 | Lim et al. |
| 2004/0208722 A1 | 10/2004 | Kuenzel |

(56) References Cited

U.S. PATENT DOCUMENTS

| | | |
|---|---|---|
| 2005/0049590 A1 | 3/2005 | Alleyne et al. |
| 2005/0053444 A1 | 3/2005 | Panasik |
| 2005/0080425 A1 | 4/2005 | Bhatnagar et al. |
| 2005/0129482 A1 | 6/2005 | Wang |
| 2005/0165398 A1 | 7/2005 | Reiley |
| 2005/0196420 A1 | 9/2005 | Zucherman et al. |
| 2005/0245929 A1 | 11/2005 | Winslow et al. |
| 2006/0036258 A1 | 2/2006 | Zucherman et al. |
| 2006/0064165 A1 | 3/2006 | Zucherman et al. |
| 2006/0064166 A1 | 3/2006 | Zucherman et al. |
| 2006/0084985 A1 | 4/2006 | Kim |
| 2006/0085070 A1* | 4/2006 | Kim .................. A61B 17/7065 623/17.11 |
| 2006/0089718 A1 | 4/2006 | Zucherman et al. |
| 2006/0095136 A1 | 5/2006 | McLuen |
| 2006/0100710 A1 | 5/2006 | Gutlin et al. |
| 2006/0182514 A1 | 8/2006 | Ito |
| 2006/0184247 A1 | 8/2006 | Edidin et al. |
| 2006/0195102 A1 | 8/2006 | Malandain |
| 2006/0241621 A1 | 10/2006 | Moskowitz et al. |
| 2006/0241770 A1 | 10/2006 | Rhoda et al. |
| 2006/0247634 A1 | 11/2006 | Warner et al. |
| 2006/0247783 A1 | 11/2006 | McKay |
| 2006/0264938 A1 | 11/2006 | Zucherman et al. |
| 2006/0264939 A1 | 11/2006 | Zucherman et al. |
| 2006/0265066 A1 | 11/2006 | Zucherman et al. |
| 2006/0265067 A1 | 11/2006 | Zucherman et al. |
| 2006/0271049 A1 | 11/2006 | Zucherman et al. |
| 2006/0271194 A1 | 11/2006 | Zucherman et al. |
| 2007/0010813 A1 | 1/2007 | Zucherman et al. |
| 2007/0032790 A1* | 2/2007 | Aschmann ......... A61B 17/7065 606/249 |
| 2007/0055291 A1 | 3/2007 | Birkmeyer et al. |
| 2007/0093830 A1 | 4/2007 | Zucherman et al. |
| 2007/0185490 A1 | 8/2007 | Implicito |
| 2007/0225706 A1 | 9/2007 | Clark et al. |
| 2007/0270840 A1 | 11/2007 | Chin et al. |
| 2008/0027438 A1 | 1/2008 | Abdou |
| 2008/0071378 A1 | 3/2008 | Zucherman et al. |
| 2008/0108990 A1* | 5/2008 | Mitchell ............ A61B 17/7068 606/305 |
| 2008/0132949 A1 | 6/2008 | Aferzon et al. |
| 2008/0147190 A1 | 6/2008 | Dewey et al. |
| 2008/0147193 A1 | 6/2008 | Matthis et al. |
| 2008/0177306 A1 | 7/2008 | Lamborne et al. |
| 2008/0183211 A1 | 7/2008 | Lamborne et al. |
| 2008/0243250 A1 | 10/2008 | Seifert et al. |
| 2008/0243254 A1 | 10/2008 | Butler |
| 2008/0253860 A1 | 10/2008 | McDuff et al. |
| 2008/0281359 A1 | 11/2008 | Abdou |
| 2008/0312741 A1 | 12/2008 | Lee et al. |
| 2008/0319481 A1 | 12/2008 | Moore |
| 2009/0054988 A1 | 2/2009 | Hess |
| 2009/0164020 A1 | 6/2009 | Janowski et al. |
| 2009/0198338 A1 | 8/2009 | Phan |
| 2009/0234389 A1 | 9/2009 | Chuang et al. |
| 2009/0254185 A1 | 10/2009 | Dollinger |
| 2009/0265006 A1 | 10/2009 | Seifert et al. |
| 2009/0281626 A1 | 11/2009 | Farr |
| 2009/0292316 A1 | 11/2009 | Hess |
| 2010/0057130 A1* | 3/2010 | Yue .................... A61B 17/7065 606/249 |
| 2010/0106190 A1 | 4/2010 | Linares |
| 2010/0106191 A1 | 4/2010 | Yue et al. |
| 2010/0114166 A1 | 5/2010 | Kohm et al. |
| 2010/0152775 A1 | 6/2010 | Seifert et al. |
| 2010/0179655 A1 | 7/2010 | Hansell et al. |
| 2010/0234889 A1 | 9/2010 | Hess |
| 2010/0318127 A1 | 12/2010 | Phan et al. |
| 2011/0066186 A1 | 3/2011 | Boyer, II et al. |
| 2011/0160773 A1 | 6/2011 | Aschmann et al. |
| 2011/0190817 A1 | 8/2011 | Thommen et al. |
| 2011/0270257 A1 | 11/2011 | Moore |
| 2012/0109203 A1 | 5/2012 | Dryer et al. |
| 2012/0109205 A1 | 5/2012 | Mitchell et al. |
| 2012/0150228 A1 | 6/2012 | Zappacosta et al. |
| 2014/0194930 A1 | 7/2014 | Hess et al. |
| 2014/0371797 A1 | 12/2014 | Seifert et al. |
| 2015/0112387 A1 | 4/2015 | Hess et al. |

FOREIGN PATENT DOCUMENTS

| | | |
|---|---|---|
| WO | WO-2008/088613 A2 | 7/2008 |
| WO | WO-2008/118907 A2 | 10/2008 |
| WO | WO-2009/132059 A1 | 10/2009 |

OTHER PUBLICATIONS

First Office Action for Chinese Patent Application No. 201480012125.4, dated Jan. 12, 2017.

International Search Report and Written Opinion for International Application No. PCT/US2016/033277, dated Sep. 14, 2016.

Medtronic: CD Horizon Spire (Trademark), Stabilization System, Information Brochure, James Robinson, MD, 2006.

St. Francis Medical Technologies, Inc., "A Patient's Guide to Lumbar Spinal Stenosis," & "X STOP (Trademark)—Interspinous Process Decompression," Information Guide, Sep. 16, 2005.

International Search Report and Written Opinion of the International Searching Authority for International Application No. PCT/US2014/0101457, dated Jun. 16, 2014.

International Preliminary Report on Patentability for PCT/US2014/01457, dated Jul. 7, 2015.

International Search Report in PCT/US08/01231 dated Aug. 29, 2008.

Written Opinion in PCT/US08/01231 dated Aug. 29, 2008.

International Search Report in PCT/US09/006742 dated Apr. 16, 2010.

Written Opinion in PCT/US09/006742 dated Apr. 16, 2010.

* cited by examiner

*Fig. 1*
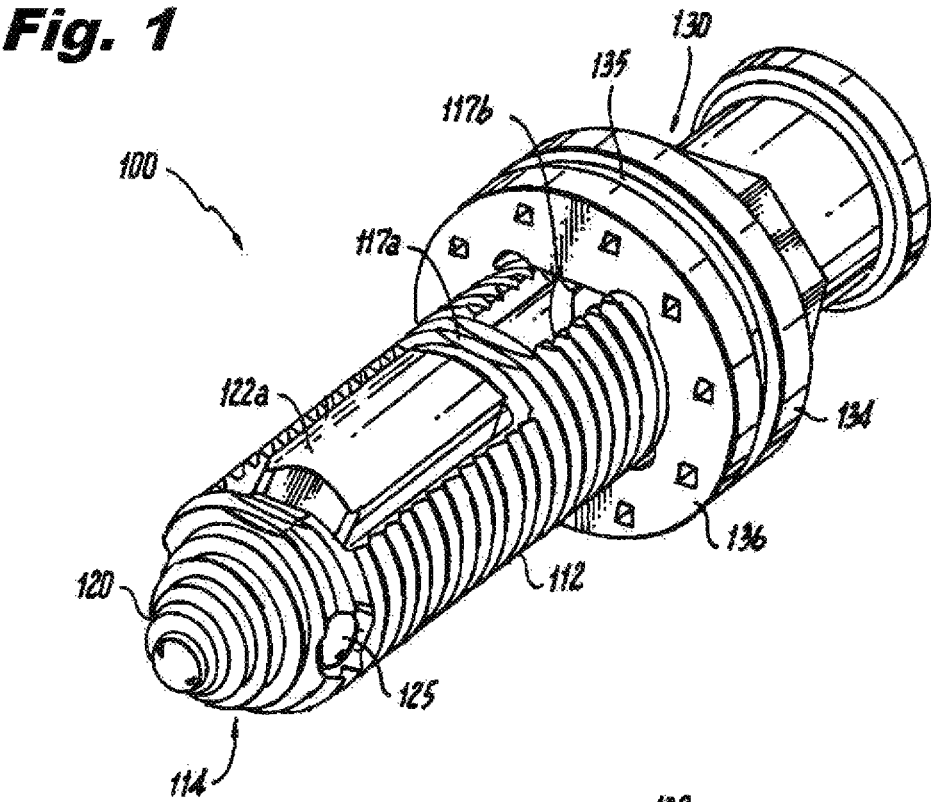
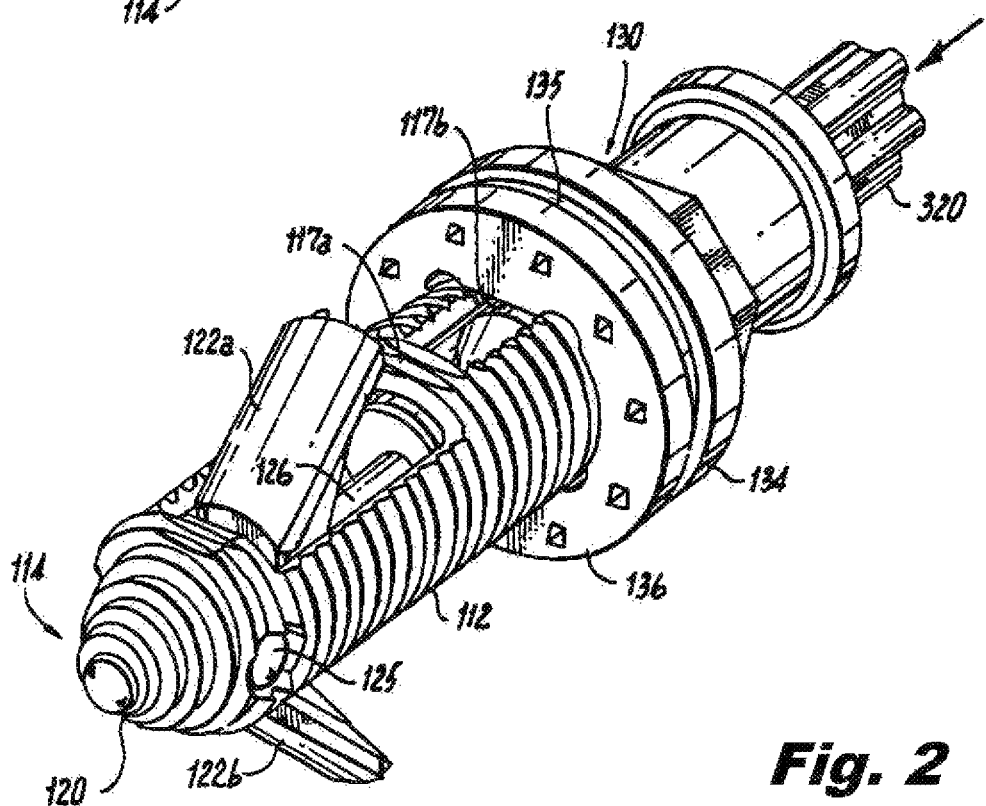
*Fig. 2*

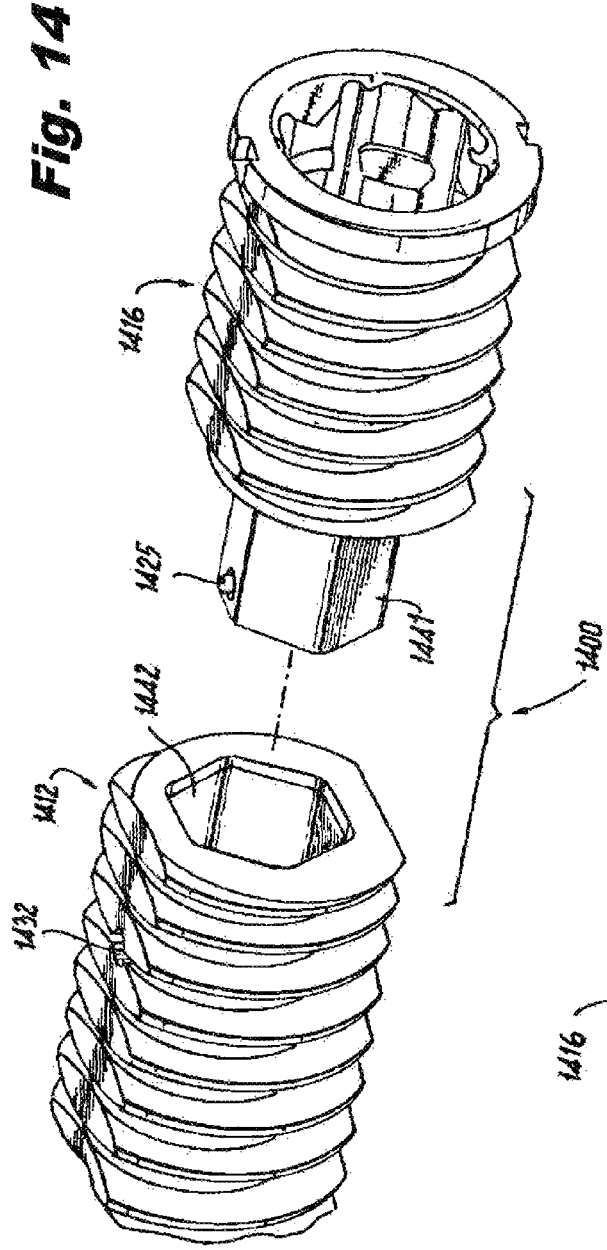
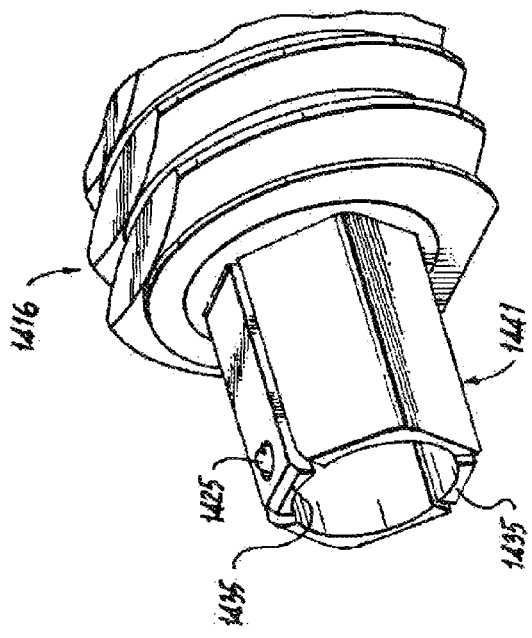

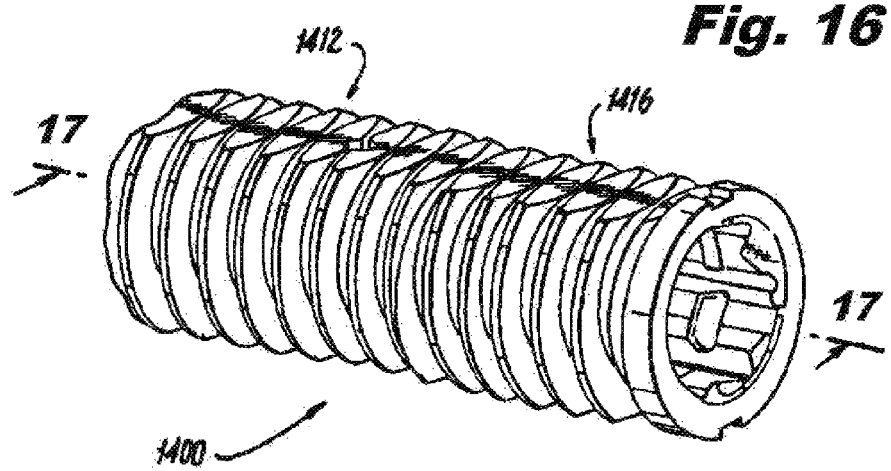
Fig. 16
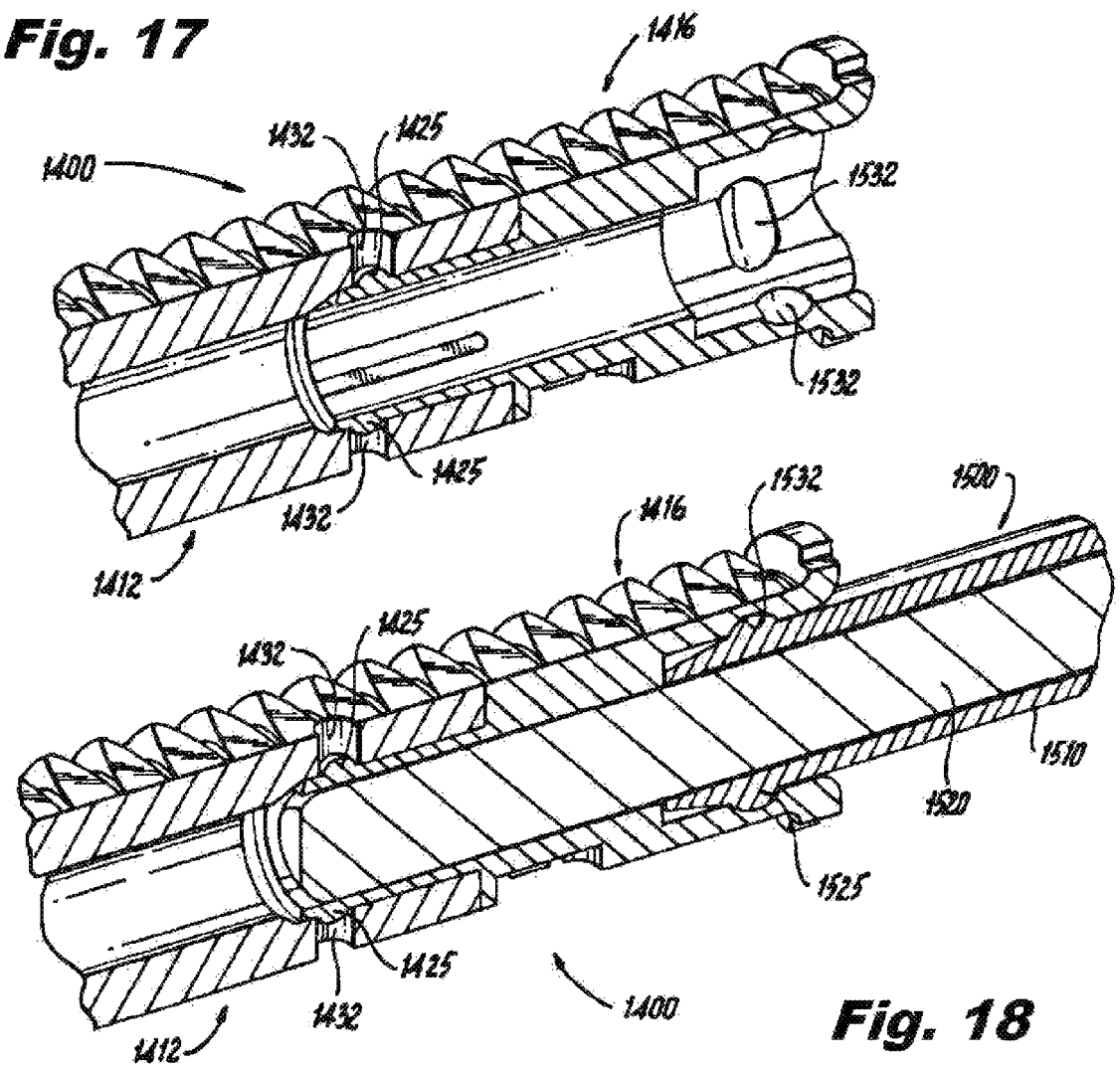
Fig. 17
Fig. 18

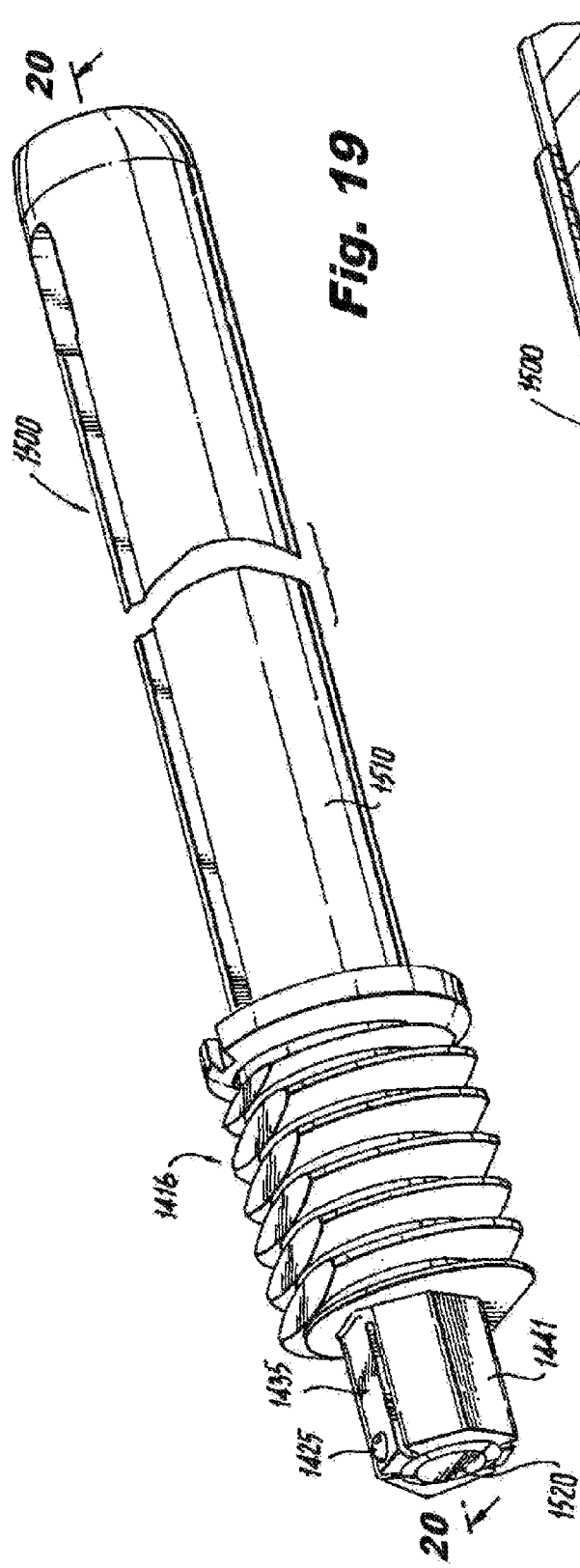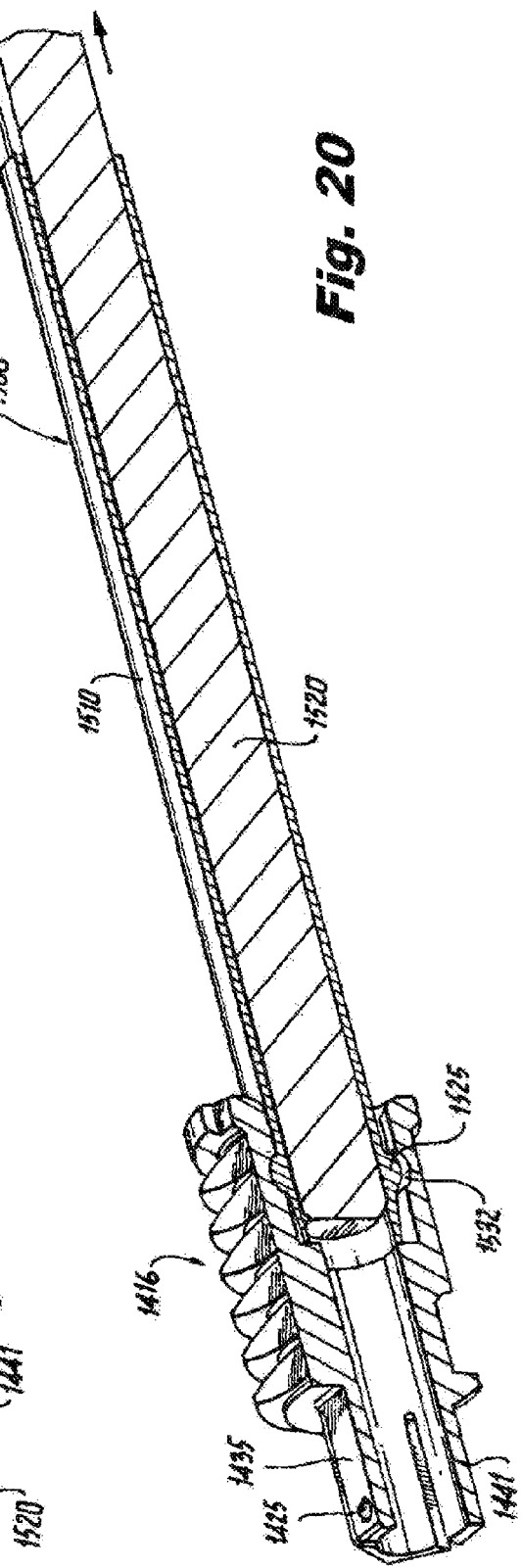

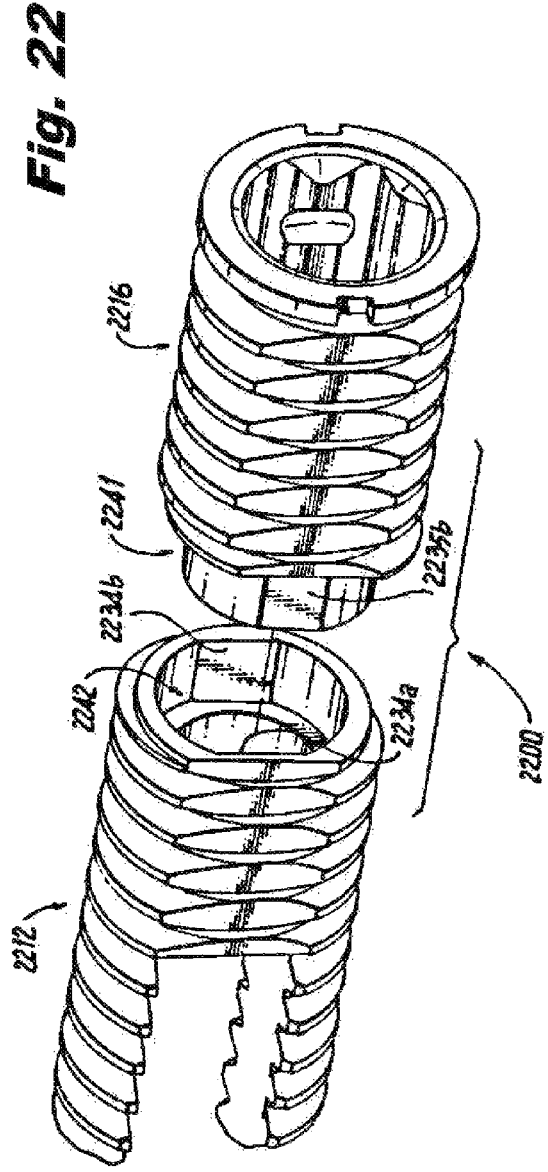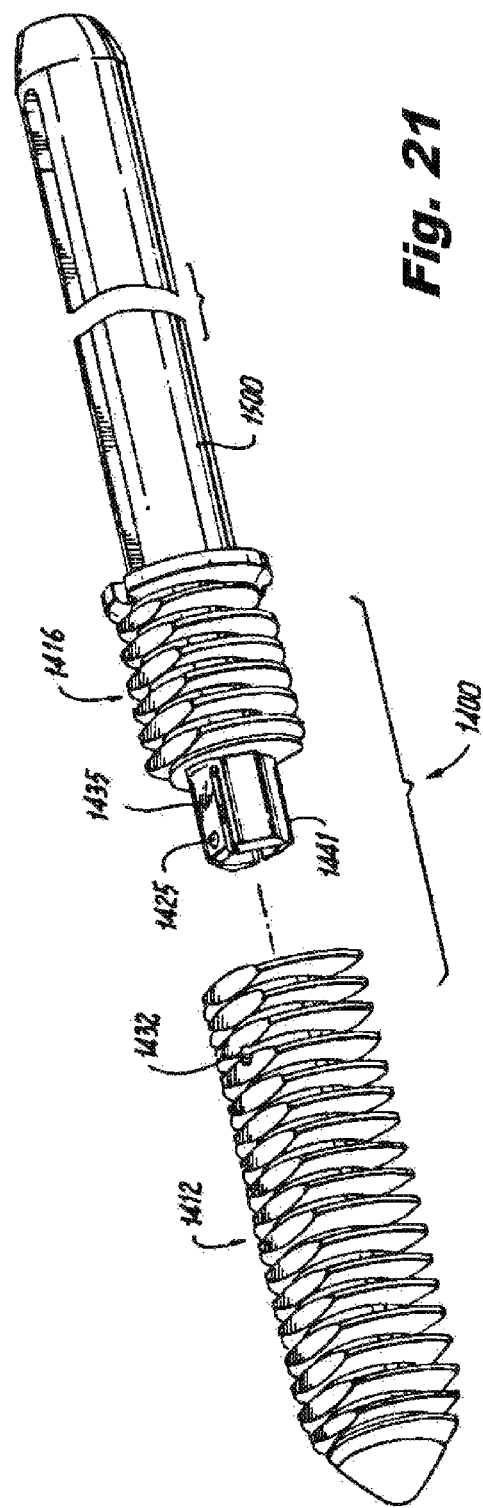

INTERSPINOUS PROCESS IMPLANT HAVING A BODY WITH A REMOVABLE END PORTION

CROSS-REFERENCE TO RELATED APPLICATIONS

The subject application claims the benefit of priority to U.S. Provisional Patent Application Ser. No. 62/165,634 filed on May 22, 2015, and it is a continuation-in-part of U.S. patent application Ser. No. 13/940,868 filed on Jul. 12, 2013, which claims the benefit of priority to U.S. Provisional Patent Application Ser. No. 61/749,595 filed on Jan. 7, 2013, and a continuation-in-part of U.S. patent application Ser. No. 15/085,687 filed on Mar. 30, 2016, which is a continuation of U.S. patent application Ser. No. 14/560,006, filed Dec. 4, 2014, now U.S. Pat. No. 9,314,276, which is a continuation of U.S. patent application Ser. No. 12/554,922 filed on Sep. 7, 2009, now U.S. Pat. No. 8,945,184, which claims the benefit of priority to U.S. Provisional Patent Application Ser. No. 61/209,997 filed on Mar. 13, 2009, the disclosures of where are all herein incorporated by reference.

BACKGROUND OF THE INVENTION

1. Field of the Invention

The subject invention is directed to spinal implants, and more particularly, to a percutaneously or posteriorly introduced spinous process implant and fusion device that has a body with a detachable proximal end portion that can be readily removed to reduce the overall length and size of the implant after it has been implanted in the patient's body.

2. Description of Related Art

The spine consists of a column of twenty-four vertebrae that extend from the skull to the hips. Discs of soft tissue are disposed between adjacent vertebrae. In addition, the spine encloses and protects the spinal cord, defining a bony channel around the spinal cord, called the spinal canal. There is normally a space between the spinal cord and the borders of the spinal canal so that the spinal cord and the nerves associated therewith are not pinched.

Over time, the ligaments and bone that surround the spinal canal can thicken and harden, resulting in a narrowing of the spinal canal and compression of the spinal cord or nerve roots. This condition is called spinal stenosis, which results in pain and numbness in the back and legs, weakness and/or a loss of balance. These symptoms often increase after walking or standing for a period of time.

There are number of non-surgical treatments for spinal stenosis. These include non-steroidal anti-inflammatory drugs to reduce the swelling and pain, and corticosteroid injections to reduce swelling and treat acute pain. While some patients may experience relief from symptoms of spinal stenosis with such treatments, many do not, and thus turn to surgical treatment. The most common surgical procedure for treating spinal stenosis is decompressive laminectomy, which involves removal of parts of the vertebrae. The goal of the procedure is to relieve pressure on the spinal cord and nerves by increasing the area of the spinal canal.

Interspinous process decompression (IPD) is a less invasive surgical procedure for treating spinal stenosis. With IPD surgery, there is no removal of bone or soft tissue. Instead, an implant or spacer device is positioned behind the spinal cord or nerves between the interspinous processes that protrude from the vertebrae in the lower back. An example of a particularly useful interspinous process implant and fusion device for treating spinal stenosis is disclosed in commonly assigned U.S. Pat. No. 9,314,276 to Hess et al., the disclosure of which is incorporated herein by reference in its entirety.

The subject invention provides an improvement over this prior art interspinous implant device, by constructing the implant body with a detachable proximal end portion that can be readily removed from the remainder of the implant body after it has been percutaneously installed and positioned by a surgeon, using a specialized tool or other device. This will advantageously reduce the overall size and profile of the device.

SUMMARY OF THE INVENTION

The subject invention is directed to a new and useful interspinous process implant that includes an elongated implant body defining a longitudinal axis and having a main body portion with opposed proximal and distal end portions, and a removable body portion operatively connected to the proximal end portion of the main body portion. The implant body is threaded along its length and further includes a distal anchor assembly and a proximal anchor assembly.

The distal anchor assembly includes two deployable anchor blades mounted for pivotal movement between a stowed position located within an interior cavity of the main body portion and a deployed position radially extending from the main body portion. The proximal anchor assembly includes an anchor collar mounted for longitudinal movement along the longitudinal axis of the implant body between a first position spaced apart from the distal anchor assembly and a second position approximated with the distal anchor assembly.

The implant further includes a locking ring threadably associated with the proximal end portion of the main body for securing the axial position of the anchor collar with respect to the elongated body. The locking ring has a pair of diametrically opposed, arcuate shaped, cantilevered pawls, each with distal facing teeth for engaging a corresponding set of teeth on a proximal facing surface of the anchor collar when the locking ring is rotated relative to the annular collar.

In one embodiment of the subject invention, the main body portion and the removable body portion are connected to one another by way of a threaded connection. For example, the main body portion has a threaded proximal bore and the removable body portion has a threaded distal shaft section for threadably engaging the threaded bore of the main body portion. Alternatively, the main body portion could have a threaded proximal shaft section for engaging with a distal threaded bore of the removable body portion.

In another embodiment of the subject invention, the main body portion and the removable body portion are connected to one another by way of a preformed frangible or separable connection, and in another embodiment the main body portion and the removable body portion are connected to one another by way of an interference or frictional fit. For example, the main body portion has a tapered bore formed in the proximal end thereof and the removable body portion has a frusto-conical end section extending from the distal end thereof for frictionally engaging the tapered bore of the main body portion. Alternatively, the main body portion has an annular reception slot formed in a proximal end thereof and the removable body portion has an annular flange extending from the distal end thereof for frictionally engaging the annular reception slot of the main body portion to create an interference fit.

In another embodiment of the invention, the main body portion and the removable body portion are connected to one another by way of a plurality of circumferentially spaced apart interlocking structures. For example, the main body portion includes a proximal bore having a set of circumferentially spaced apart radially inwardly projecting hemispherical protuberances for engaging a corresponding set of circumferentially spaced apart radially inwardly extending hemi-spherical or rounded recesses formed on a distal stem of the removable body portion. Alternatively, the main body portion includes a bore having a set of circumferentially spaced apart radially outwardly projecting hemi-spherical or rounded recesses for engaging a corresponding set of circumferentially spaced apart radially outwardly extending hemi-spherical protuberances formed on a distal stem of the removable body portion.

Furthermore, the circumferentially spaced apart interlocking structures perform the task of transmitting the forces applied axially, laterally and torsionally from the removable body portion of the implant to the main body portion of the implant. The structures are formed such that the main body and removable body portion are only engaged in one orientation, enabling the threads on the exterior of the main body portion and the removable body portion to be timed such that the rotating members of the proximal anchor assembly can pass from one to the other In an embodiment of the invention, the proximal bore in the main body portion has a polygonal cross-section and the distal stem of the removable body portion has a corresponding polygonal cross-section. This interface can be square or hexagonal, for example. In addition, each of the hemi-spherical protuberances on the distal stem of the removable body portion may be defined by spring loaded detent or ball. Alternatively, each of the hemi-spherical protuberances on the distal stem of the removable body portion may be located on an integrally formed flexible cantilevered tab or the like.

In another embodiment of the subject invention, the main body portion has a proximal bore with diametrically opposed flattened anti-rotation walls and the removable body portion has a distal stem with corresponding diametrically opposed flattened anti-rotation surfaces. In yet another embodiment of the subject invention, the main body portion and the removable body portion are connected to one another by way of a ratchet connection. More particularly, the main body portion includes a pair of diametrically opposed, arcuate shaped, cantilevered pawls, each with proximally facing teeth for engaging a corresponding set of teeth on a distal facing surface of the removable body portion upon rotation of the removable body portion relative to the main body portion of the implant.

In another embodiment of the subject invention, a longitudinally moving proximal anchor assembly is mounted on the main body portion. The proximal anchor assembly includes a plate with spike features that engage the spinous process bone, and is slideably mounted on the threaded body; and a rotating nut, which is engaged with the main body and removable body thread. The plate and nut are engaged with each other such that the plate does not rotate with the nut, but remains positioned relative to nut as the longitudinal position of the nut tracks along the threaded body axis. Furthermore, the thread profile of the main body thread and the removable body thread may be external contoured such that any relative movement of one portion to another does not impede the longitudinal travel of the nut along the thread, should there exist differentiating lateral forces on main body portion and removable body portion during movement of the nut.

It is also envisioned that the removable body portion of the implant could be made of a biological material that can be readily absorbed by a patient's body, such that the disconnection of the removable body portion from the main body portion occurs over time without mechanical intervention, which is well within the intended scope of the subject invention. It is further envisioned that the main body portion and the removable body portion are operatively connected to one another by way of an insertion instrument that spans a common interior bore extending through the implant. It is also envisioned that the removable body portion can be carried within a tool adapter.

The interspinous process implant of the subject invention further includes an actuation assembly disposed within the implant body for selectively deploying the distal anchor assembly, wherein the actuation assembly includes a plunger body mounted for longitudinal movement between a proximal position and a distal position. Preferably, the plunger body includes an annular spring for releasably engaging an annular groove formed within an interior cavity of the removable body portion, and the plunger body extends across the interface between the removable and main body portions. The removable and main body interface contains a mechanical interlock which the plunger body blocks movement of, mechanically connecting the removable body portion to the main body portion. Accordingly, movement of the plunger body from its proximal position to its distal position to deploy the distal anchor assembly, further results in free motion in the mechanical interlock, allowing the disconnection of the removable body portion from the main body portion by an externally applied force.

In an alternative embodiment, the plunger body includes a proximal annular spring for releasably engaging an annular groove formed within an interior cavity of the removable body portion and a distal annular spring for releasably engaging an annular groove formed within the interior cavity of the main body portion, to mechanically connect the releasable body portion to the main body portion. Moreover, the plunger body of the actuation assembly preferably prevents separation of the main body portion and the removable body portion when disposed in a first position, and allows separation of the main body portion and the removable body portion when disposed in a second position.

In accordance with an embodiment of the subject invention, the removable body portion includes a pair of distally extending arcuate torque transmitting tabs for engaging interlocking arcuate channels formed in a proximal end of the main body portion for transmitting applied forces from the removable body portion to the main body portion. Preferably, the interlocking torque transmitting tabs and channels are dimensioned and configured such that the main body portion and the removable body portion are only engaged in one orientation, enabling threads on the exterior of the main body portion and the removable body portion to be timed such that the proximal anchor assembly can threadably transition between the body portions.

It is also envisioned that the anchor collar and the locking ring of the proximal anchor assembly can be operatively connected to one another to in such a manner so as to allow relative rotation of the anchor collar and locking ring. In addition, it is envisioned that the threaded implant body could be profiled such that the threading does not impede a rotationally engaged member to longitudinally move from the removable body portion to main body portion, if misalignment exists between the two body portions.

The subject invention is also directed to a method of implanting an interspinous process implant comprising the steps of positioning an elongated implant body in a patient's body between two adjacent spinous processes, wherein the implant body includes a main body portion with opposed proximal and distal end portions, and a removable body portion operatively connected to the proximal end portion of the main body portion, disconnecting the removable body portion of the implant body from the main body portion of the implant body, and then removing the removable body portion from the patient's body.

The method further includes the steps of deploying a distal anchor assembly from a stowed position within an interior cavity of the main body portion and moving a proximal anchor assembly along a longitudinal axis of the implant body between a first position spaced apart from the distal anchor assembly and a second position approximated with the distal anchor assembly.

These and other features of the implant of the subject invention and the manner in which it is manufactured and employed will become more readily apparent to those having ordinary skill in the art from the following enabling description of the preferred embodiments of the subject invention taken in conjunction with the several drawings described below.

BRIEF DESCRIPTION OF THE DRAWINGS

So that those skilled in the art to which the subject invention relates will readily understand how to make and use the interspinous process implant of the subject invention without undue experimentation, embodiments thereof will be described in detail herein below with reference to certain figures, wherein:

FIG. 1 is a perspective view of an interspinous process implant constructed in accordance with an exemplary embodiment of the subject invention, showing the blades of the distal anchor assembly in a stowed position;

FIG. 2 is a perspective view of the implant of FIG. 1, with the blades of the distal anchor assembly in a radially deployed position;

FIG. 14 is a perspective view of the main body portion and removable body portion separated from one another and showing a mechanical connection there between that includes a hexagonal stem and bore, where the stem includes an interlocking protuberance.

FIG. 15 is an enlarged perspective view of the distal end portion of the removable body portion the implant wherein the stem includes a diametrically opposed cantilevered tabs each containing a protuberance that fits within a corresponding recess in the bore of the main body portion;

FIG. 16 is a perspective view of a section of the implant body wherein the main body portion and the removable body portion are connected to one another;

FIG. 17 is a cross-sectional view taken along line 17-17 of FIG. 16 illustrating the internal features of the main body portion and the removable body portion;

FIG. 18 is a cross-section view as in FIG. 17, showing a two part insertion instrument within the interior bore of the implant body, which aides in the mechanical connection of the main body portion and the removable body portion through interlocking protuberances and recesses associated therewith;

FIG. 19 is perspective view of the removable body portion of the implant supported, with the plunger portion of the insertion instrument extended into the stem of the removable body portion to prevent the flexible cantilevered tabs from flexing inward;

FIG. 20 is a cross-sectional view taken along line 20-20 of FIG. 19, but with the plunger portion of the insertion instrument retracted to allow the flexible tabs to collapse, thereby allowing disconnection of the removable body portion from the main body portion of the implant;

FIG. 21 is a perspective view illustrating the disconnection of the removable body portion of the implant from the main body portion of the implant by way of the interlocked insertion/removal tool, in accordance with the structural arrangement depicted in FIGS. 16-20;

FIG. 22 is a perspective view of the removable body portion separated from the main body portion, wherein the distal stem of the removable body portion and the proximal bore of the main body portion includes cooperating laterally opposed anti-rotation surface features;

DETAILED DESCRIPTION OF THE PREFERRED EMBODIMENTS

Figure 3:
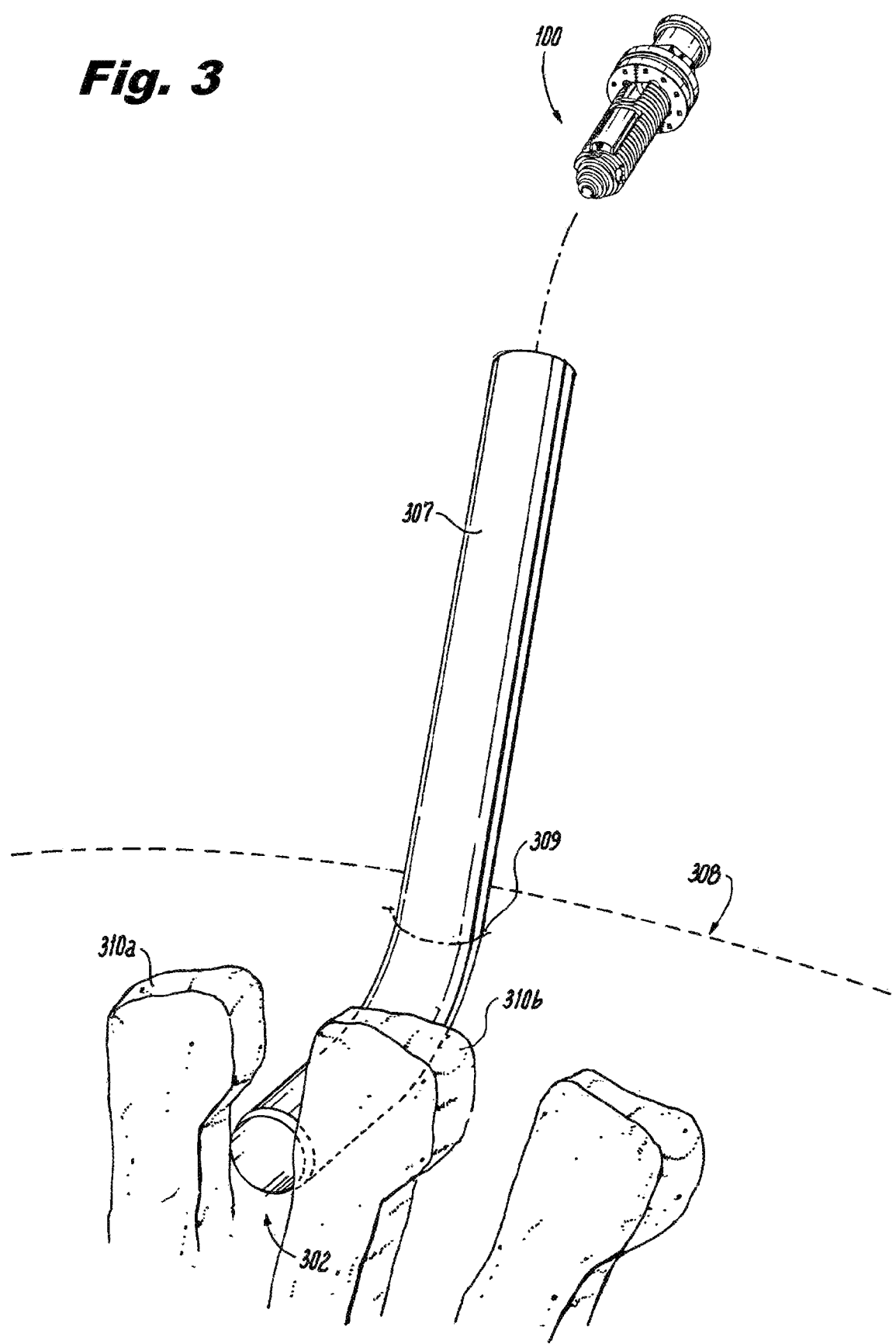
FIG. 3 is an illustration of the implant of FIG. 1 during percutaneous deployment through an introducer tube.

Referring now to the drawings, wherein like reference numerals identify similar structural features or aspects of the subject invention, there is illustrated in FIG. 1 a new and unique interspinous implant designated generally by reference numeral 100. The implant 100 is particularly well adapted for use in performing minimally invasive surgical procedures for treating damage of the intervertebral discs and/or the vertebral members.

It is envisioned however, that the implant 100 of the subject invention can be used in other spinal procedures as well, including, but not limited to as an adjunct to spinal fusion procedures, or as a spinal stabilization device. Those skilled in the art will readily appreciate from the following description that the interspinous process implant 100 of the subject invention is well adapted for percutaneous insertion. That is, the implant 100 is dimensioned and configured for introduction and placement both through a small lateral skin incision; and also through a posterior open approach. The lateral approach will be described in more detail hereinbelow.

Referring to FIGS. 1 and 2, the interspinous process implant 100 includes an elongated threaded body portion 112 having a distal end portion 114 and an opposing proximal end portion 116. The body portion 112 can be configured as a solid element or alternatively it can be at least partially hollow, and may include a plurality of longitudinal openings (not shown) to permit insertion of demineralized bone or another type of osteogenesis-promoting substance or fusion adjunct material, and can also promote the ingrowth of bone.

The implant 100 further includes a threaded conical head portion 120, which is associated with a distal end portion 114. The head portion 120 is dimensioned and configured to progressively distract two adjacent spinous processes as the implant 100 is advanced there between, which will be discussed in more detail below with respect to FIGS. 3 through 7.

It is to be understood, however, that the head portion 120 facilitates insertion of the implant 100, when distraction is initially performed by a separate instrument. It is also to be understood that the elongated body portion 112 can alternatively be provided without threads, in accordance with an alternative aspect of the invention.

With continuing reference to FIGS. 1 and 2, the implant device 100 further includes a proximal anchor assembly 130 that is operatively associated with the threaded body 112.

The anchor assembly 130 includes an anchor collar 134, a threaded locking ring 136 and an interposed lock washer 135. The anchor assembly 130 is configured for longitudinal movement along the length of body 112 between a first position spaced from the head portion 120 and second position approximated with the head portion 120.

It is envisioned that the operative connection between the body portion 112 and the proximal anchor assembly 130 can be accomplished in a variety of ways including a direct threaded engagement between the proximal anchor assembly 130 and the body 112 or through the use of a captured threaded nut that permits the proximal anchor assembly 130 to translate longitudinally along the threaded body portion 112 without rotating about the axis of the body portion 112, such as by providing diametrically opposed interfacing flat regions 117a, 117b associated with the body 112 and the anchor assembly 130.

The distal end portion 114 of the implant 100 includes a distal anchor assembly consisting of two radially-deployable blades 122a, 122b adapted for engaging adjacent spinous processes. The blades 122a, 122b pivot about a pin 125 between a stowed position shown in FIG. 1 and a deployed position shown in FIG. 2 through activation of an internal plunger 126 controlled by an insertion tool 320. When deployed, the blades 122a, 122b of the distal anchor assembly function in concert with the proximal anchor assembly 130 for engaging adjacent spinous processes. Further details regarding the structure and function of the implant are disclosed in commonly assigned U.S. Pat. No. 9,314,276, which is incorporated herein by reference in its entirety.

Referring to FIG. 3 through 7, there is illustrated the basic operative steps for percutaneously placing the implant 100 through an incision 309 in a patient 308 at a targeted interspinous process space 302 between two adjacent spinous processes 310a and 310b using a introducer sleeve 307. The insertion method can include the use of a stylet, dilators, and the like to gain access and define an operative path for the sleeve 307. Moreover, dorsal percutaneous insertion of the implant 100 can be accomplished as set forth, for example, in commonly assigned U.S. Pat. No. 8,075,593, which is incorporated herein by reference in its entirety.

In general, insertion of a stylet forms an entry path, along which one or more dilators can be sequentially advanced, in order to dilate soft tissues between the incision and the target interspinous process space 302. The sleeve 307 can then be advanced through the entry path. After inserting the sleeve 307, a distracter, which can be a tap (e.g., a graduated tap as disclosed in U.S. Pat. No. Des. 692,562) can then be inserted and advanced into the target interspinous process space 302, to tap and gradually distract the adjacent spinous processes 310a, 310b and/or help determine an appropriate size of implant to be inserted.

Figure 4:
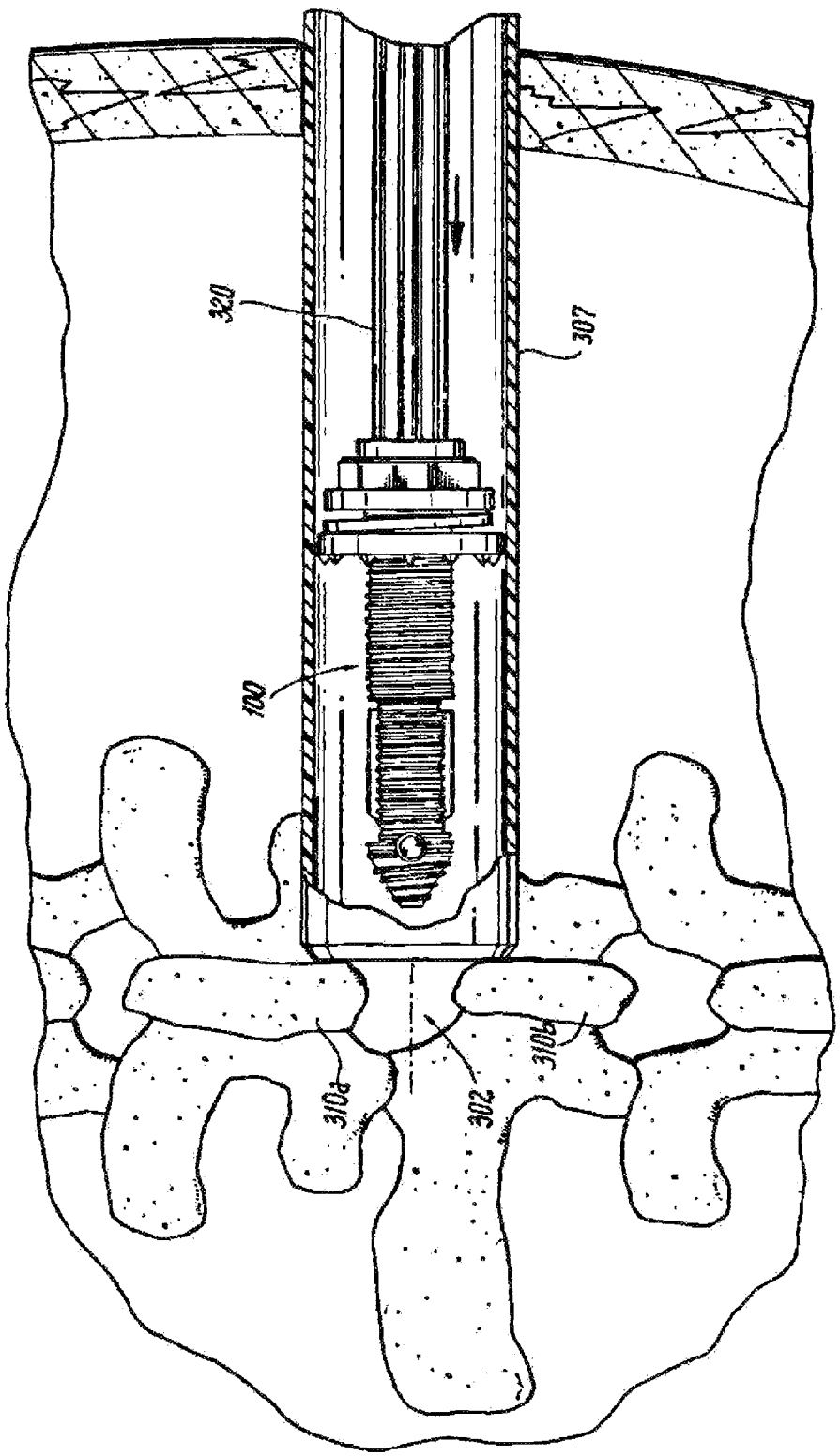
FIG. 4 is an enlarged view of the distal end portion of the percutaneous introducer tube with the implant positioned therein prior to insertion between adjacent spinous processes.
Figure 5:
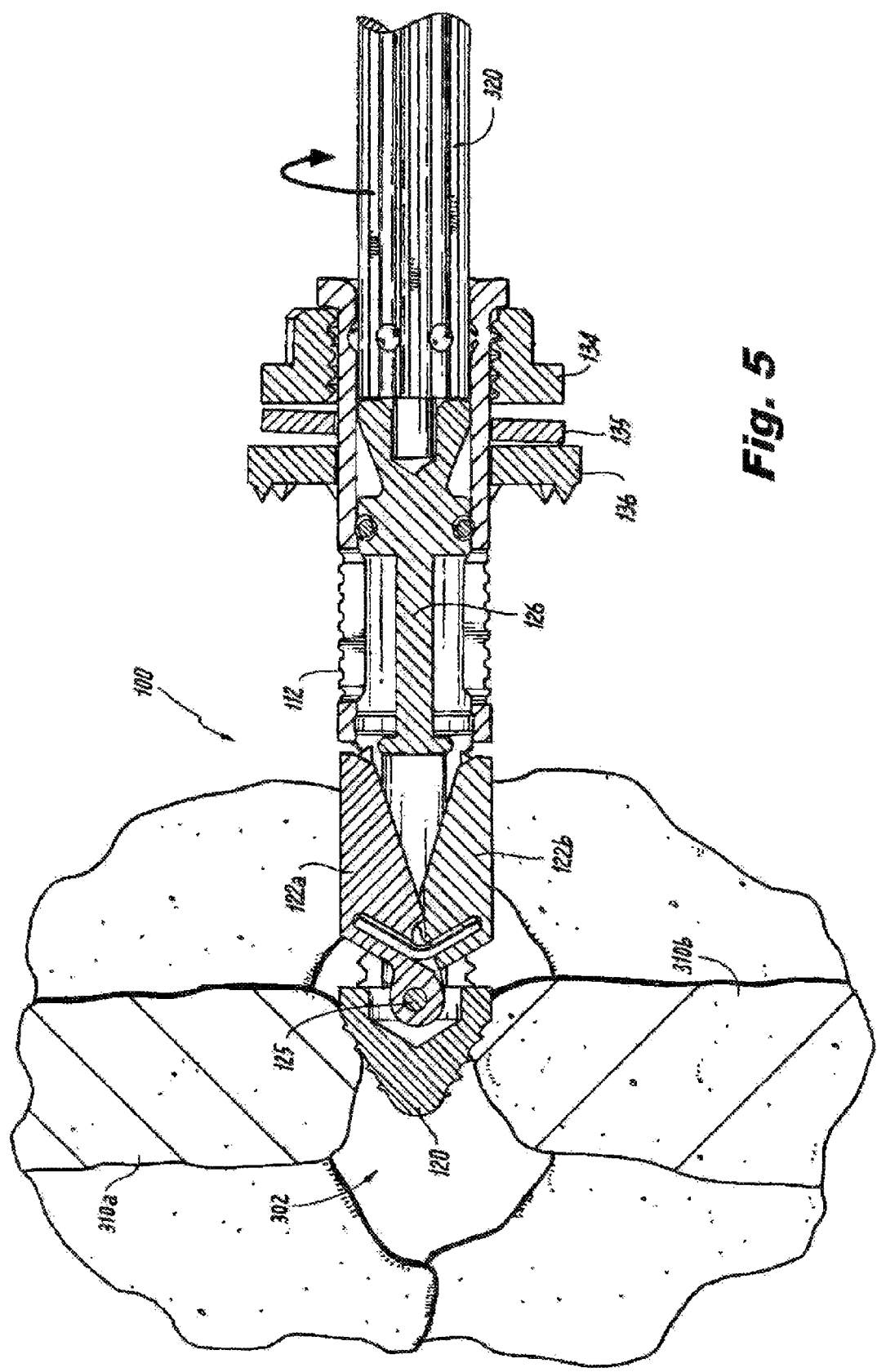
FIG. 5 shows the implant in cross-section as it is threadably inserted into a targeted interspinous process space.
Figure 6:
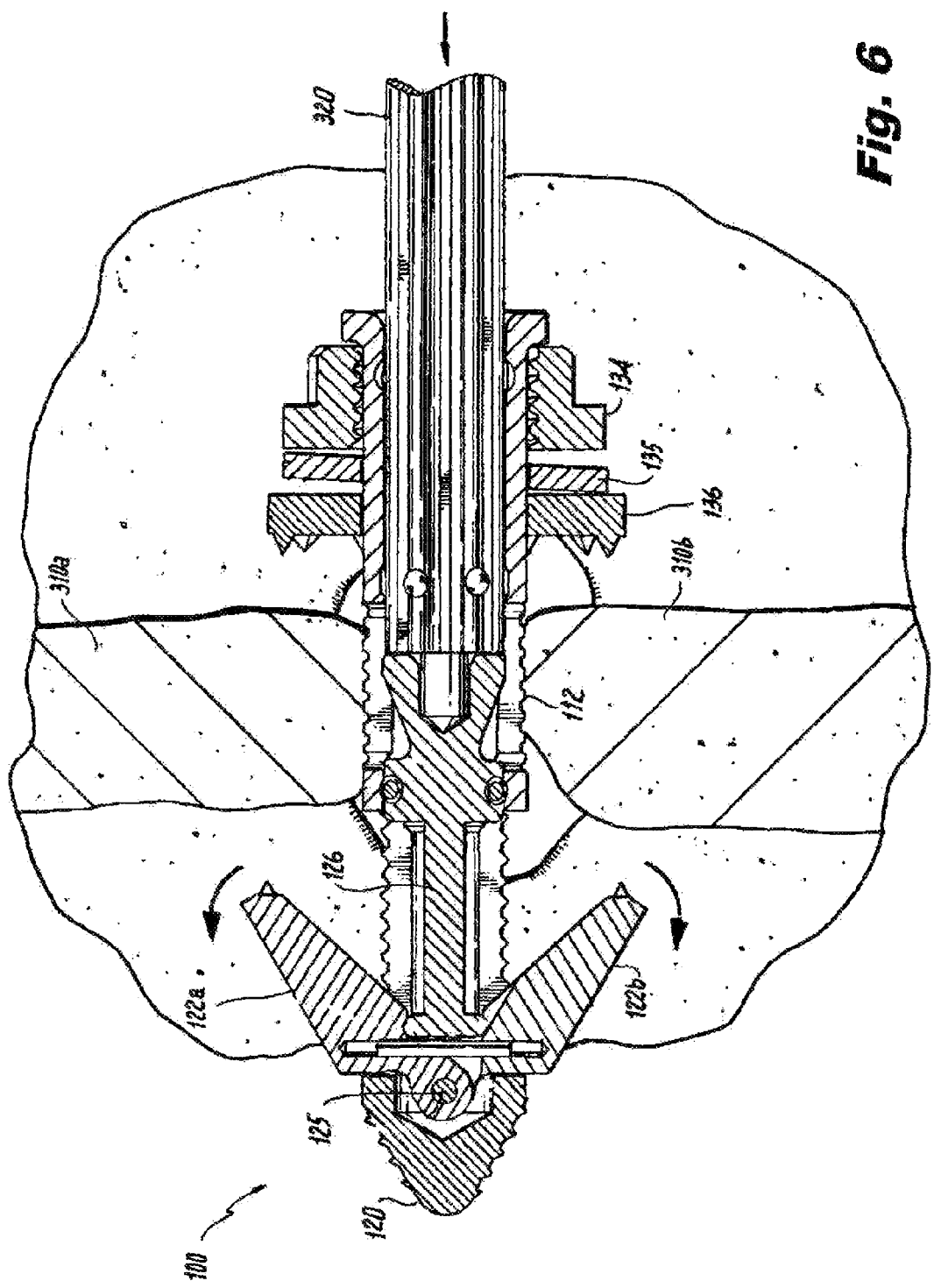
FIG. 6 shows the implant in cross-section with the internal plunger assembly moved in a distal direction to effect the radial deployment of the distal anchor blades.

Following selection of an implant 100 having a size appropriate for a desired amount of interspinous distraction, the implant 100 can be inserted, held by the insertion tool 320, advanced through the sleeve 307, up to the target interspinous process space 302, as best seen in FIG. 4. Then, as shown in FIG. 5, the implant 100 is laterally advancing to the target interspinous process space 302, under application of a rotational force applied by the insertion tool 320, by virtue of the threads provided on the body 112 thereof. Once in position, internal plunger 126 located within the interior cavity of the implant body 112 is urged distally by the insertion device 320, effecting radial deployment of the distal anchor blades 122a and 122b about pin 125, as shown in FIG. 6.

Figure 7:
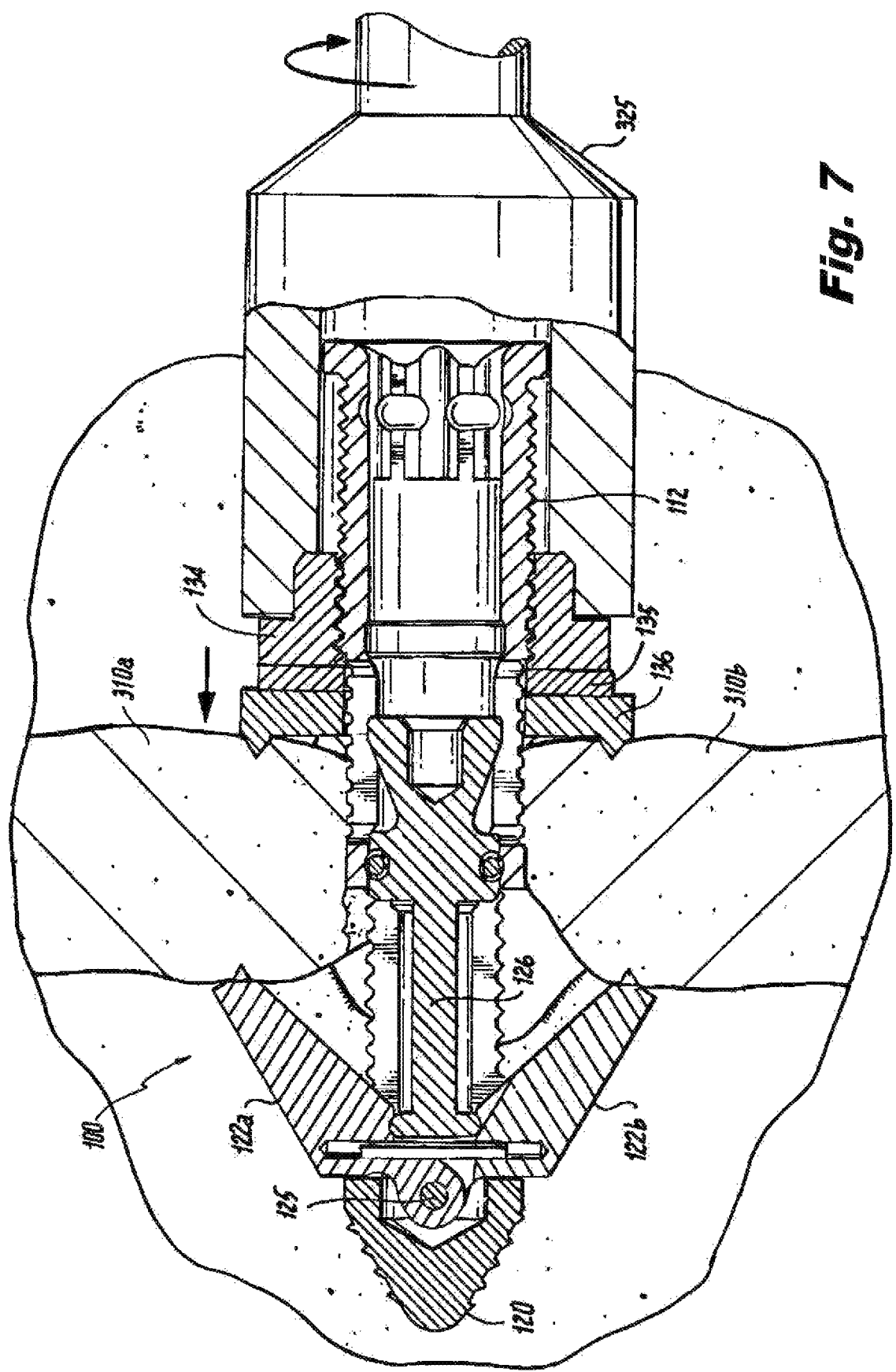
FIG. 7 shows the implant in cross-section with the proximal anchor element and associated locking ring moved in a distal direction into approximation with the distal anchor assembly, thereby engaging the adjacent spinous processes.

The spiked anchor collar 134 of proximal anchor assembly 130 is then approximated toward the distal anchor blades 122a, 122b of the distal anchor assembly by rotating a threaded locking collar 136 relative to the implant body 112 using the insertion tool 320, as shown in FIG. 7. This action draws the implant body 112 proximally, thereby urging the spiked tips of blades 122a, 122b to securely engage the adjacent bony structure of the spinous processes 310a, 310b.

In accordance with embodiments of the subject invention, it is envisioned and entirely within the scope of the subject disclosure that the implant body can be constructed from two interconnected body portions. That is, the implant body can include a main body portion that would remain positioned in the patient's body for distraction of the spinous process and a removable body portion that can be disconnected or otherwise detached from the main body portion after implantation and deployment, and subsequently removed from the patient's body. This will effectively lessen the amount of material remaining in the patient's body.

It is envisioned that the removable body portion can be made from a biologic material which can be absorbed by the patient's body over time. For example, the removable body portion can be made from biphasic calcium phosphate or a poly lactic acid (PLDLA). Thus, the separation of the two interconnected body portions can be accomplished without mechanical intervention. In other embodiments of the subject invention, the removable body portion is mechanically connected to the main body portion, as discussed in more detail hereinbelow, with reference to FIGS. 8 through 35.

Figure 8:
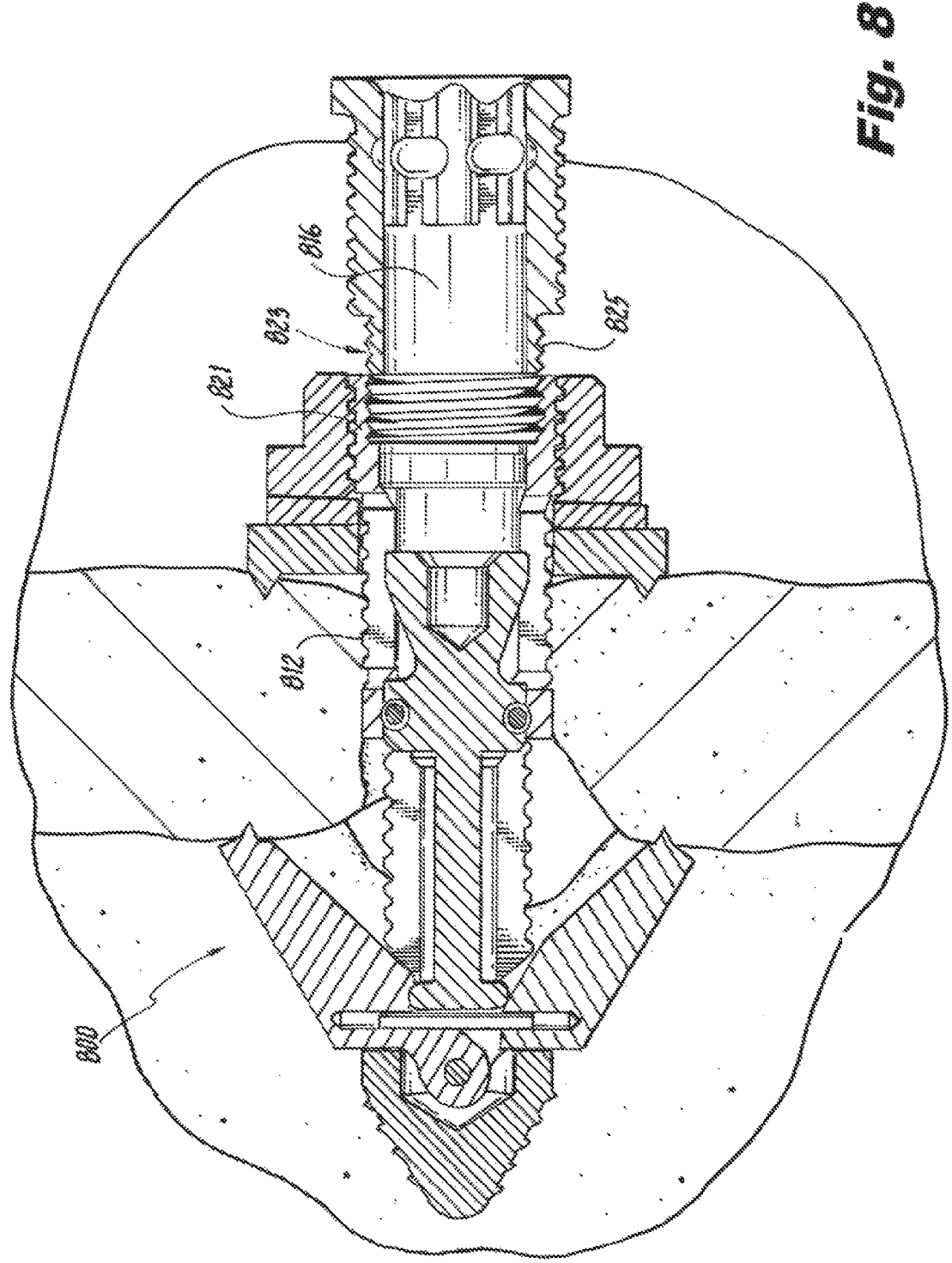
FIG. 8 shows another embodiment of the implant of the subject invention in an installed position between two adjacent spinous processes, wherein the implant body includes a main body portion and a removable body portion that are threadably connected to one another.

Referring to FIG. 8, there is illustrated another implant constructed in accordance with an embodiment of the subject invention and designated generally by reference numeral 800 that includes a main body portion 812 and a removable body portion 816 that are connected to one another by way of a threaded connection. For example, the main body portion 812 has a threaded proximal bore 821 and the removable body portion 816 has a threaded distal shaft or stem section 825 for threadably engaging the threaded proximal bore 821 of the main body portion 812. Importantly, the external thread form that cooperates with the threaded locking ring 834 of the proximal anchor assembly 830 extends continuously between the proximal section of the main body portion 812 and the removable body portion 816, as if they were one integral component.

The removable body portion 816 includes a proximal reception bore 850 for receiving and engaging an insertion tool 320, as shown for example in FIG. 5. As illustrated in FIG. 8, after the distal anchor blades 822a, 822b of the distal anchor assembly have been deployed by plunger 826 and the proximal anchor assembly 830 has been approximated with the distal anchor assembly, the removable body portion 816 is disconnected from the main body portion 812 to reduce the length of the implant 800. It is also envisioned that the main body portion 812 of implant 800 could have a threaded proximal shaft section for engaging with a distal threaded bore of the removable body portion 816.

Figure 9:
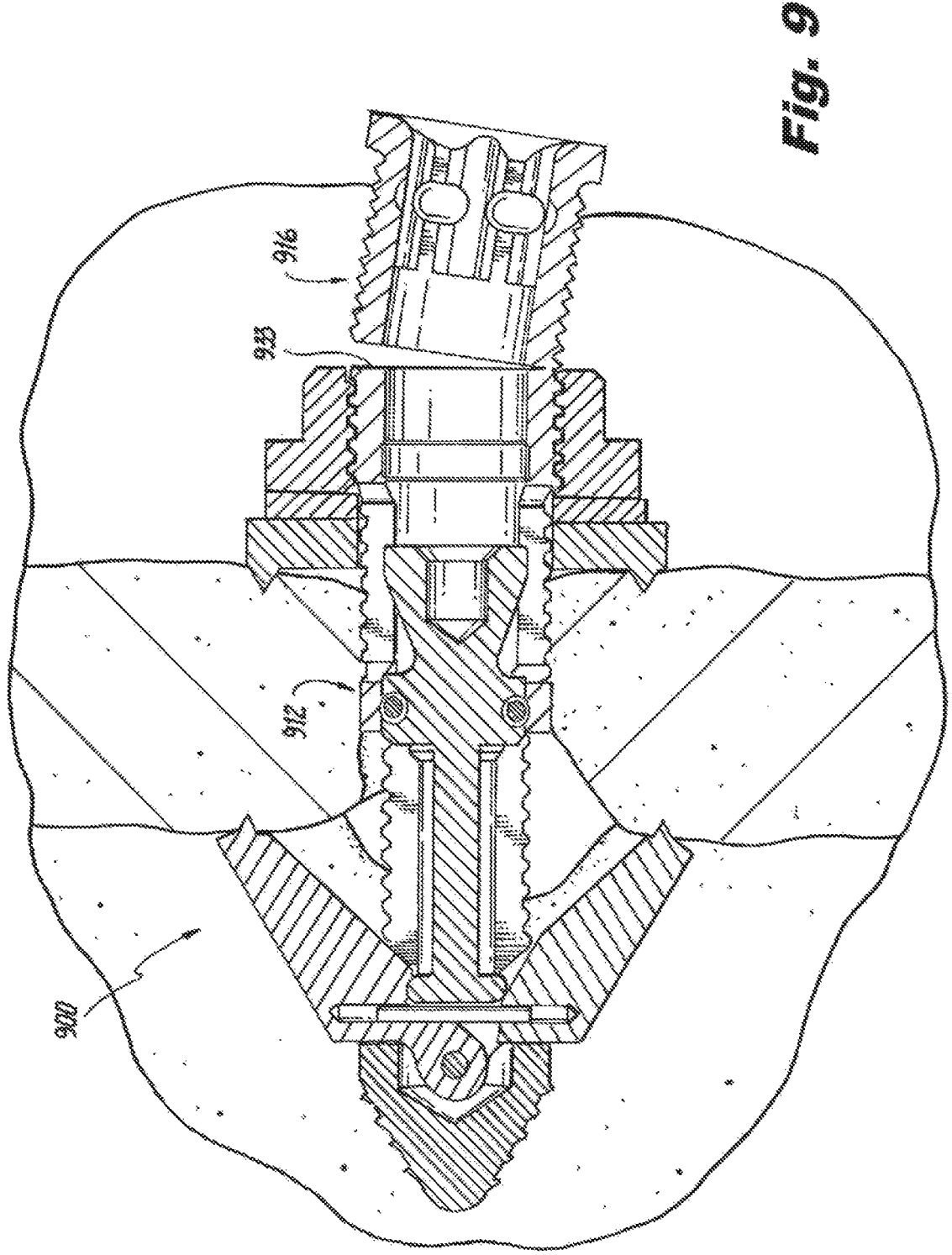
FIG. 9 shows another embodiment of the implant of the subject invention wherein the main body portion and a removable body portion are connected to one another along a preformed frangible or separable mechanical parting line.

Referring to FIG. 9, there is illustrated an implant designated generally by reference numeral 900 that includes a main body portion 912 and a removable body portion 916 that are connected to one another by way of a preformed frangible or separable connection located along a parting line 933. Here, once the implant 900 has been installed, the removable body portion 916 can be severed from the main body portion 912 and removed by the surgeon to advantageously reduce the length of the implant 900.

Figure 10:
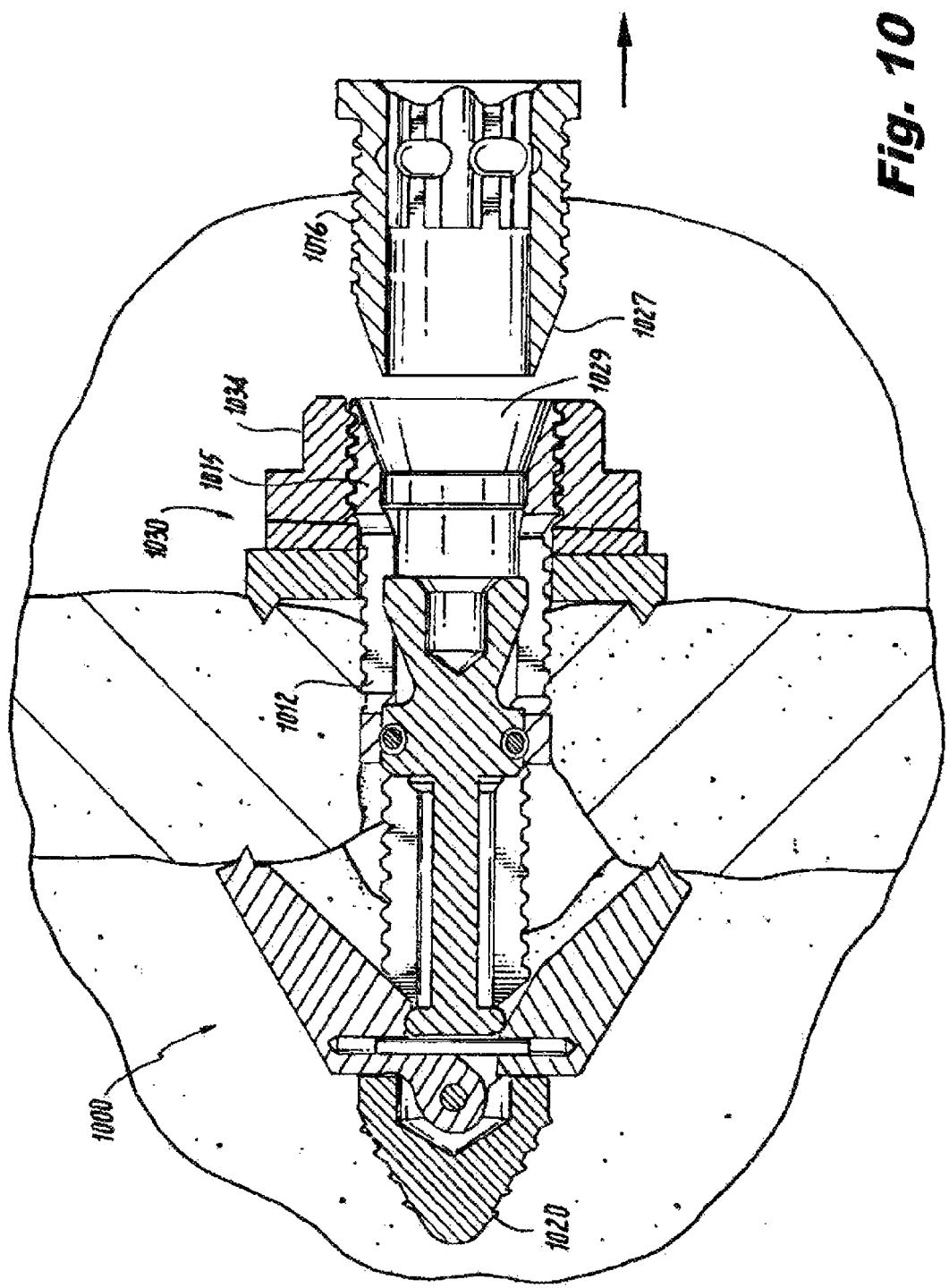
FIG. 10 shows another embodiment of the implant of the subject invention wherein the main body portion and a removable body portion are connected to one another by way of an interference or frictional fit.

Referring to FIG. 10, there is illustrated another embodiment of the implant designated generally by reference numeral 100 which includes a main body portion 1012 and a removable body portion 1016 that are connected to one another by way of an interference or compression fit, which is aided by the threaded engagement of the locking collar 1034 of proximal anchor assembly 1030 with the proximal threaded section 1015 of the main body portion 1012.

For example, as shown in FIG. 10, the main body portion 1012 has a tapered bore 1029 formed in the proximal end thereof and the removable body portion 1016 has a frusto-conical end section 1027 extending from the distal end thereof for frictionally engaging the tapered bore 1029 of the main body portion 1012. When the proximal anchor assembly is in a proximal-most position, it serves to compress the end section 1027 within the tapered bore 1029. After the implant 1000 has been deployed and the proximal anchor assembly 1030 has been approximated toward the distal end 1020 of the main body portion 1012 of implant 1000, there will be less compressive force on the end section 1027 of the removable body portion 1016, and it can be readily disconnected from the tapered proximal bore 1029 in main body portion 1012 to advantageously reduce the length of the implant 1000.

Figure 13:
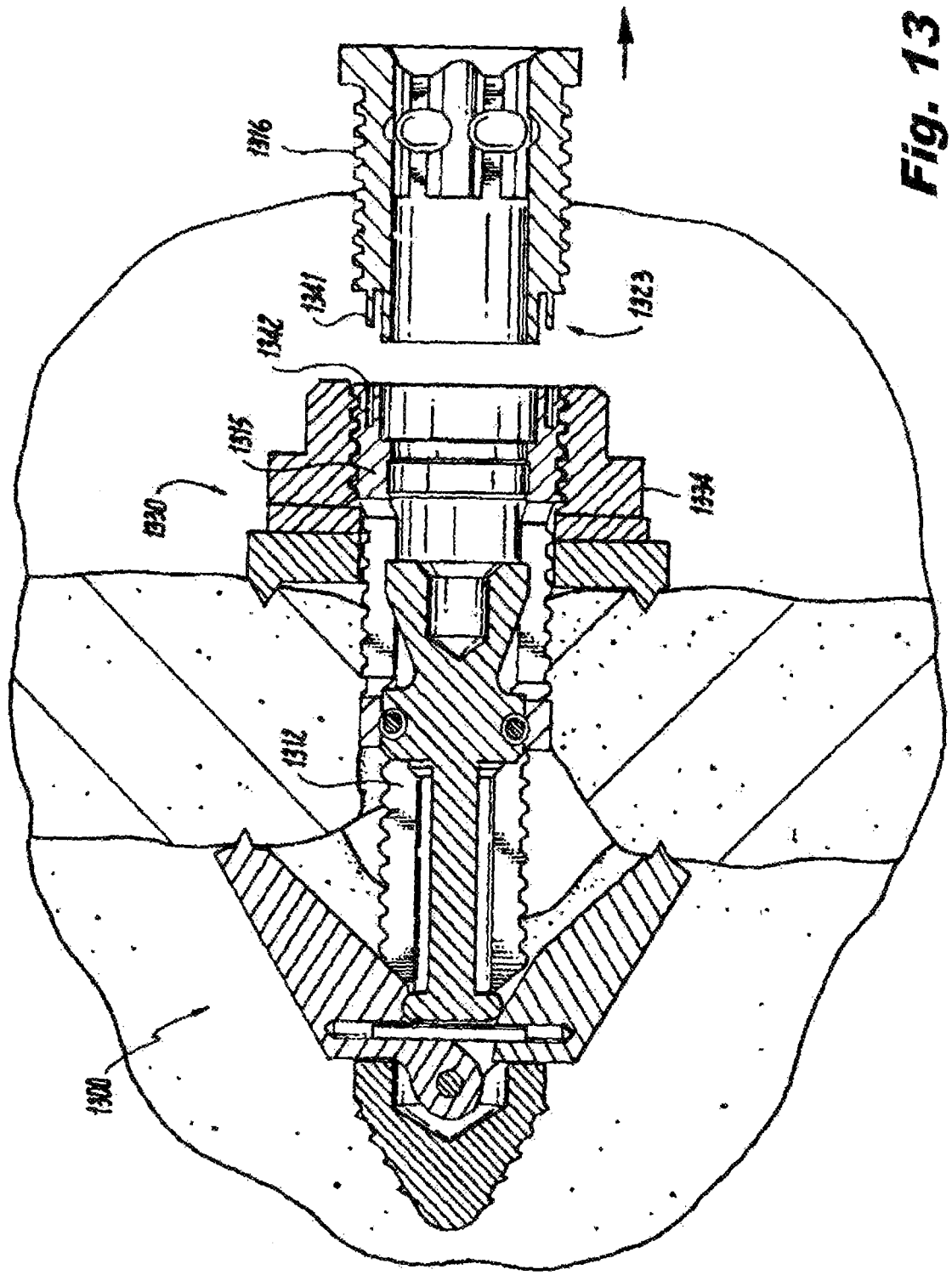
FIG. 13 shows another embodiment of the implant of the subject invention wherein the main body portion has an annular reception slot formed in a proximal end thereof and the removable body portion has an annular flange extending from the distal end thereof for frictionally engaging the annular reception slot of the main body portion.

Referring ahead to FIG. 13, there is illustrated another implant 1300 that has a compression or interference fit, wherein the main body portion 1312 has an annular reception slot 1342 formed in a proximal end thereof and the removable body portion 1316 has an annular flange 1341 extending from the distal end thereof for intimately and frictionally engaging the annular reception slot 1342 of the main body portion 312 to create an interference fit. This interference fit is enhanced by the threaded interaction of the proximal anchor assembly 1330 with the main body portion 1312, as described above with respect to implant 1000. It is envisioned that the annular reception slot in the main body portion and the annular flange on the removable body portion can be configured as one or more inter-fingering arcuate slot and flange sections.

Figure 11:
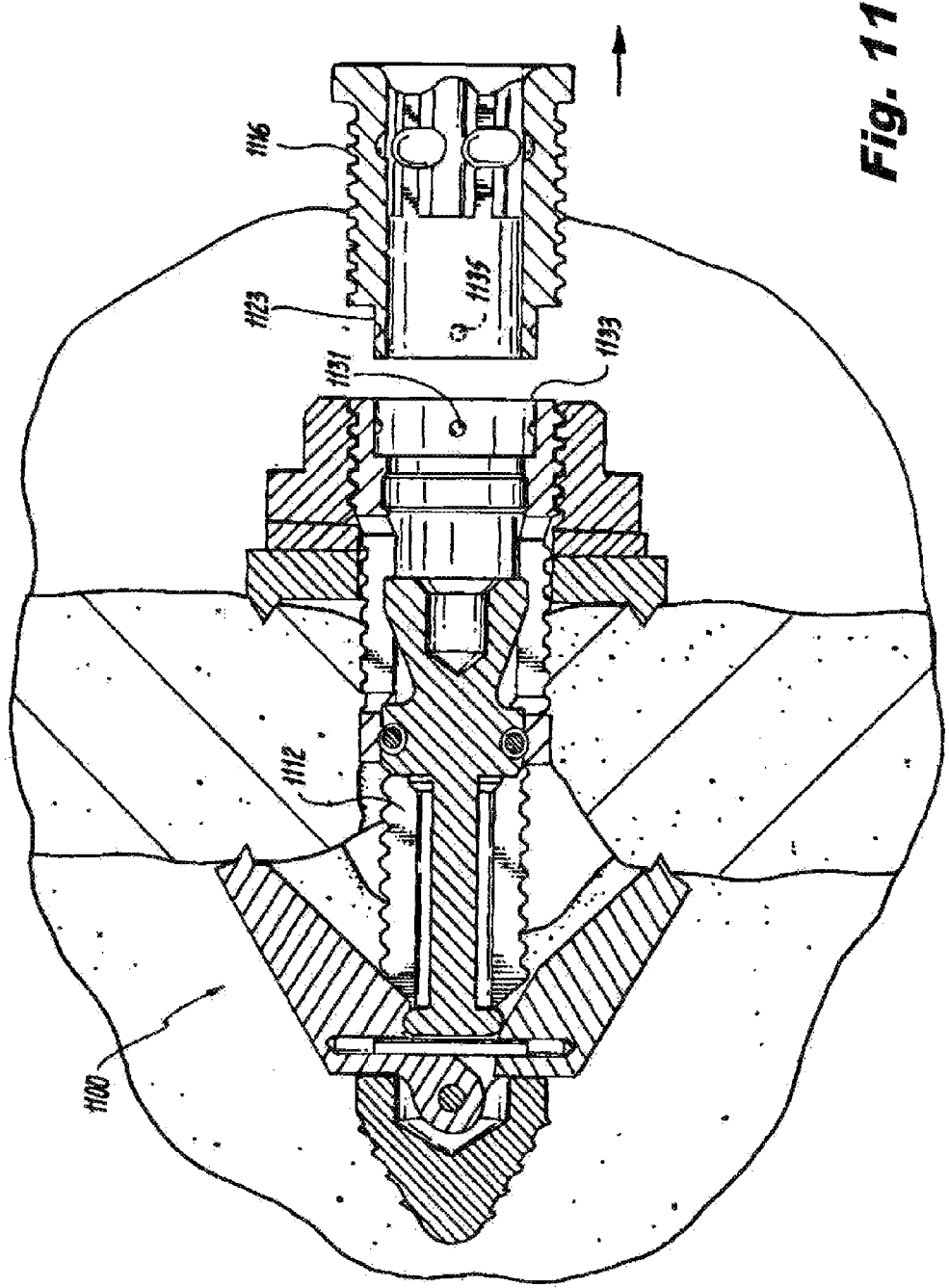
FIG. 11 shows another embodiment of the implant of the subject invention wherein the main body portion and the removable body portion are connected to one another by a plurality of circumferentially spaced apart interlocking structures including protuberances associated with the main body portion and recesses associated with the removable body portion.

Referring back now to FIGS. 11 and 12, in other embodiments of the invention the main body portion and the removable body portion are connected to one another by way of a plurality of circumferentially spaced apart interlocking structures. For example, as shown in FIG. 11, there is shown an implant 1100 wherein the main body portion 1112 includes a proximal bore 1133 having a set of circumferentially spaced apart radially inwardly projecting hemispherical protuberances 1131 for positively engaging a corresponding set of circumferentially spaced apart radially inwardly extending hemi-spherical or rounded recess 1135 formed on a distal stem 1123 of the removable body portion 1116.

Figure 12:
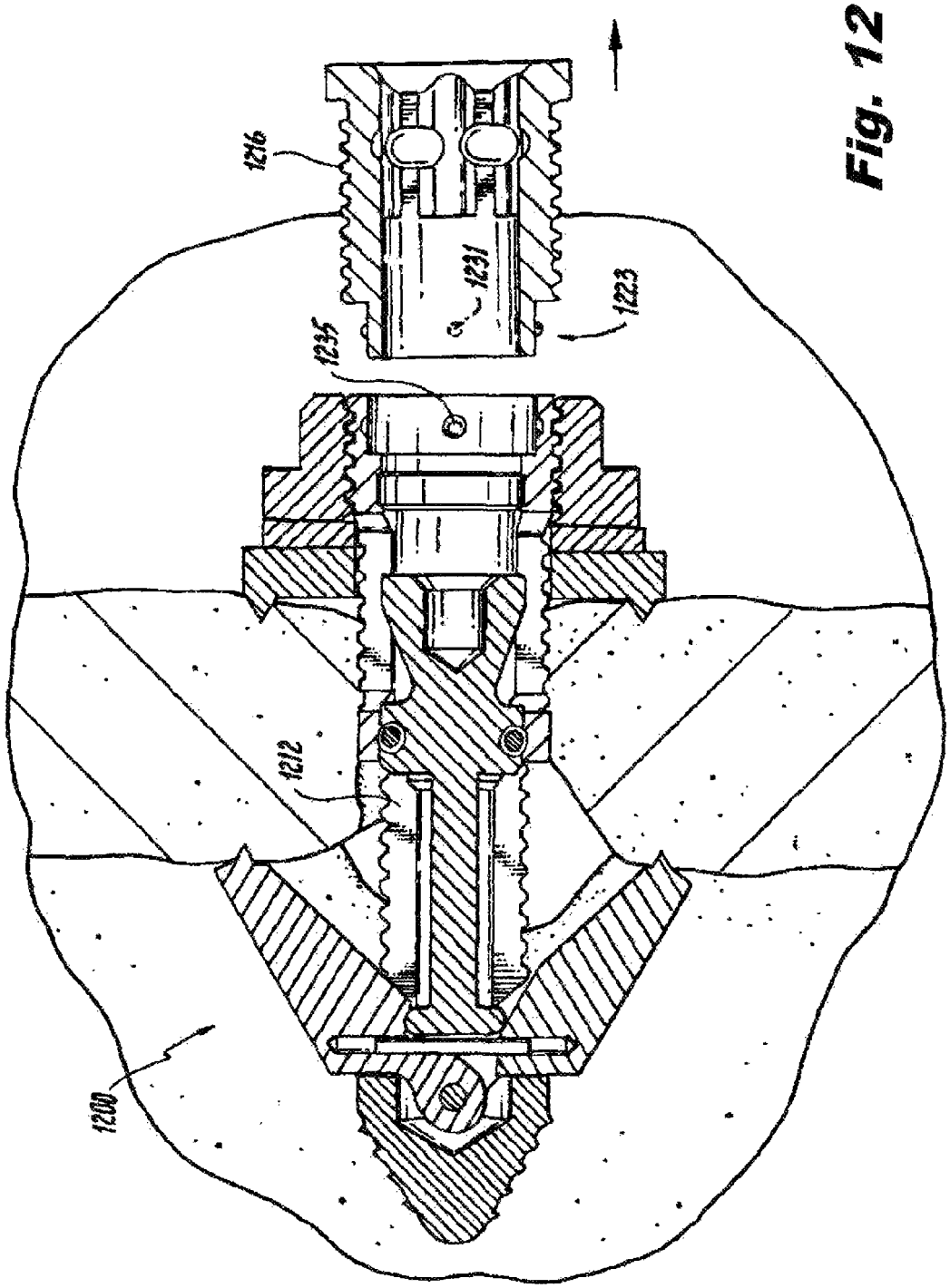
FIG. 12 shows yet another embodiment of the implant of the subject invention wherein the main body portion and the removable body portion are connected to one another by a plurality of circumferentially spaced apart interlocking structures including recesses associated with the main body portion and protuberances associated with the removable body portion.

Alternatively, as shown in FIG. 12, the main body portion 1212 of implant 1200 includes a proximal bore 1233 having a set of circumferentially spaced apart radially outwardly projecting hemi-spherical or rounded recesses 1235 for engaging a corresponding set of circumferentially spaced apart radially outwardly extending hemi-spherical protuberances 1231 formed on a distal stem 1223 of the removable body portion 1216. In both of embodiments shown in FIGS. 11 and 12, the threaded interaction of the locking ring of the proximal anchor assembly with the proximal section of the main body portion will serve to enhance the mechanical connection through radial compression.

Referring now to FIG. 14, in an embodiment of the implant designated by reference numeral 1400, the proximal bore 1442 in the main body portion 1412 has a polygonal cross-section and the distal stem 1441 of the removable body portion 1416 has a corresponding polygonal cross-section that fit together mechanically. This mechanical interface can be square or hexagonal, for example. In addition, one or more a hemi-spherical spring detents or spherical balls 1425 may be associated with the distal stem 1441 of the removable body portion 1416 for cooperative engagement with corresponding apertures or recess 1432 in the main body portion 1412 of implant body 1400.

Alternatively, as shown in FIGS. 15-21, the hemi-spherical protuberances or detents 1425 on the distal stem 1441 of the removable body portion 1416 may be located on an integrally formed diametrically opposed flexible cantilevered tabs 1435 that fit within corresponding diametrically opposed recesses 1432 in the bore 1442 of the main body portion 1412 when the implant body 1400 is interconnected as shown in FIGS. 16 and 17.

Referring now to FIG. 18, a two part insertion instrument 1500 is disposed within the interior bore of the implant body 1400, to aide in the mechanical connection of the main body portion 1412 and the removable body portion 1416. More particularly, the insertion instrument 1500 includes an outer sleeve portion 1510 and an inner plunger portion 1520 that translates relative to the outer sleeve portion 1520. The distal end section of the outer sleeve portion 1510 includes circumferentially disposed radially outwardly extending protuberances 1525 for releasable interconnection with correspondingly disposed recesses 1532 formed in the proximal bore 1450 of the removable body portion 1416.

When the plunger portion 1520 is in a distal-most position as shown for example in FIGS. 18 and 19, it prevents the flexible cantilevered tabs 1435 from deflecting radially inward, maintaining the mechanical connection between the main body portion 1412 and the removable body portion 1416. When the plunger portion 1520 of the insertion instrument 1500 is retracted as shown in FIG. 20, the flexible tabs 1435 can readily deflect, thereby allowing disconnection of the removable body portion 1416 from the main body portion 1412 of the implant 1400. The removable body portion 1416 of the implant 1400 can then be disconnected from the main body portion 1412 of the implant by way of the interlocked insertion/removal tool 1500, as shown in FIG. 21.

Figure 23:
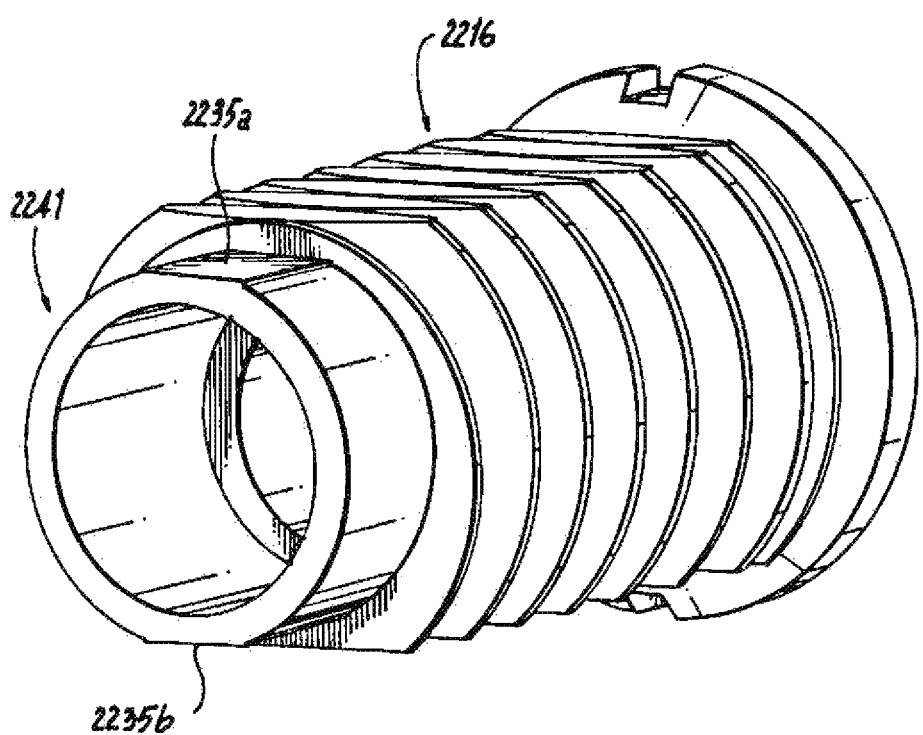
FIG. 23 is a perspective view of removable body portion of the implant, as configured in FIG. 22 with anti-rotation features.
Figure 24:
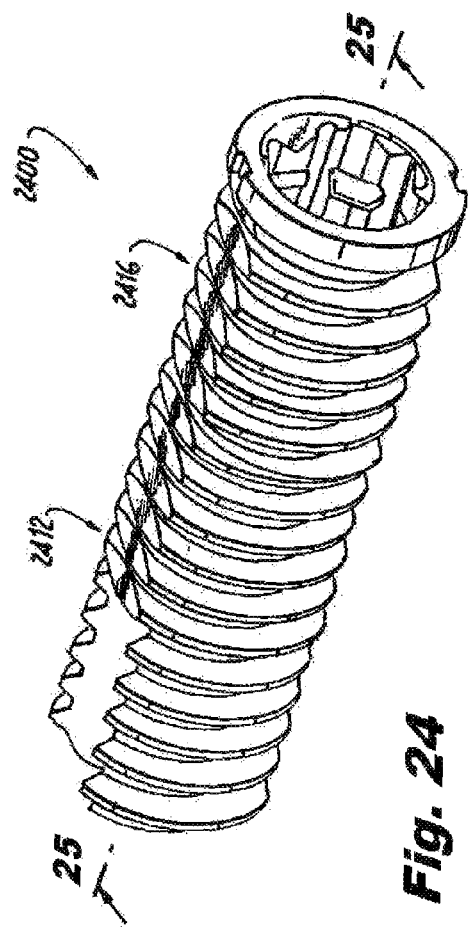
FIG. 24 is a perspective view of a section of the threaded implant body, wherein the removable end portion is mechanically connected to the main body portion by way of an internal actuation plunger used to deploy the distal anchor blades (which are not shown)
Figure 25:
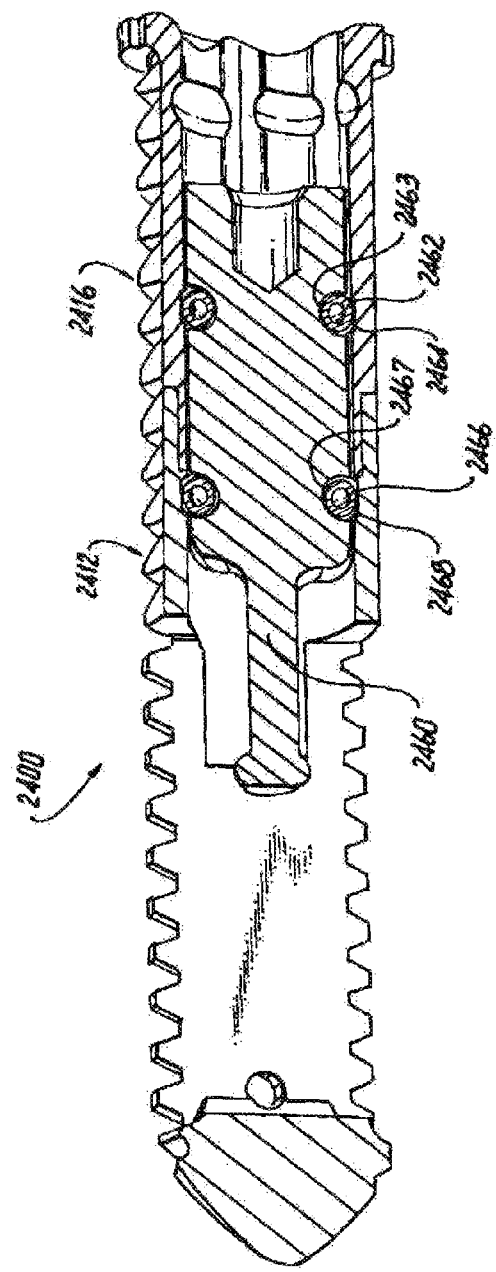
FIG. 25 is a cross-sectional view of the implant taken along line 25-25 of FIG. 24, wherein the plunger is in a proximal position to facilitate the mechanical connection between the removable body portion and the main body portion through a pair of annular springs that seat within corresponding annular grooving.
Figure 26:
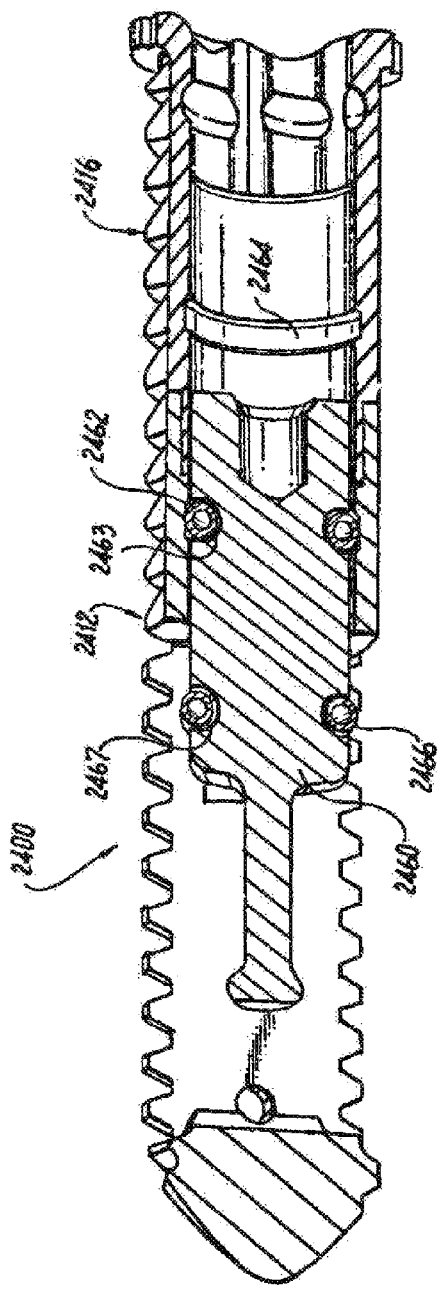
FIG. 26 is a cross-sectional view of the implant taken along line 25-25 of FIG. 24, wherein the plunger is in a distal position to facilitate the disconnection of the removable body portion and the main body portion.

Referring now to FIGS. 22 and 23, there is illustrated yet another implant body designated generally by reference numeral 2200 that employs an interference or compression fit connection, wherein the main body portion 2212 has a proximal bore 2242 with diametrically opposed flattened anti-rotation walls 2234*a* and 2234*b*, and the removable body portion 2216 has a distal stem 2241 with corresponding diametrically opposed flattened anti-rotation surfaces 2235*a* and 2235*b*. This connection is preferably enhanced or otherwise aided by the position and compressive action of the proximal anchor assembly (not shown) relative to the anti-rotation features.

Referring to FIGS. 24 through 27, there is illustrated still another two-part implant body constructed in accordance with an embodiment of the subject invention and designated generally by reference numeral 2400, which includes a main body portion 2412 having a proximal reception bore 2142 and a removable body portion 2416 having a distal stem 2441, that are mechanically connected to one another by way of an internal actuation plunger used to deploy the distal anchor blades (not shown). More particularly, the implant body 2400 includes an actuation plunger 2460 mounted for longitudinal movement between a proximal position shown in FIG. 25 and a distal position shown in FIG. 26.

Figure 27:
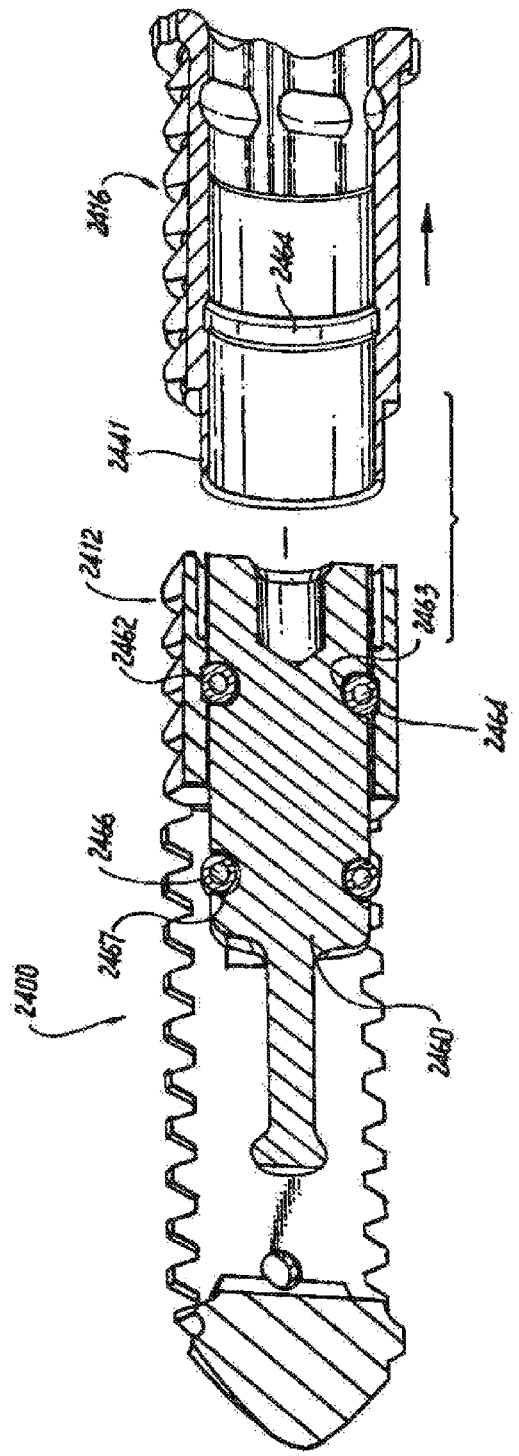
FIG. 27 shows separation of the removable body portion from the main body portion shown in FIGS. 25 and 26.

The plunger 2460 includes a proximal annular spring 2462 seated in an annular slot 2463 for releasably engaging an annular groove 2464 formed within an interior cavity of the removable body portion 2416 and a distal annular spring 2466 seated in an annular slot 2467 for releasably engaging an annular groove 2468 formed within the interior cavity of the main body 2412 portion, to mechanically connect the removable body portion 2416 to the main body portion 2412. In operation, movement of the plunger 2460 from its proximal position in FIG. 25 to its distal position in FIG. 26 disengages the proximal annular spring from annular groove 2460 in removable body portion 2416, disconnecting the removable body portion 2416 from the main body portion 2412, and permitting subsequent separation of the two structures from one another, as shown in FIG. 27.

Figure 28:
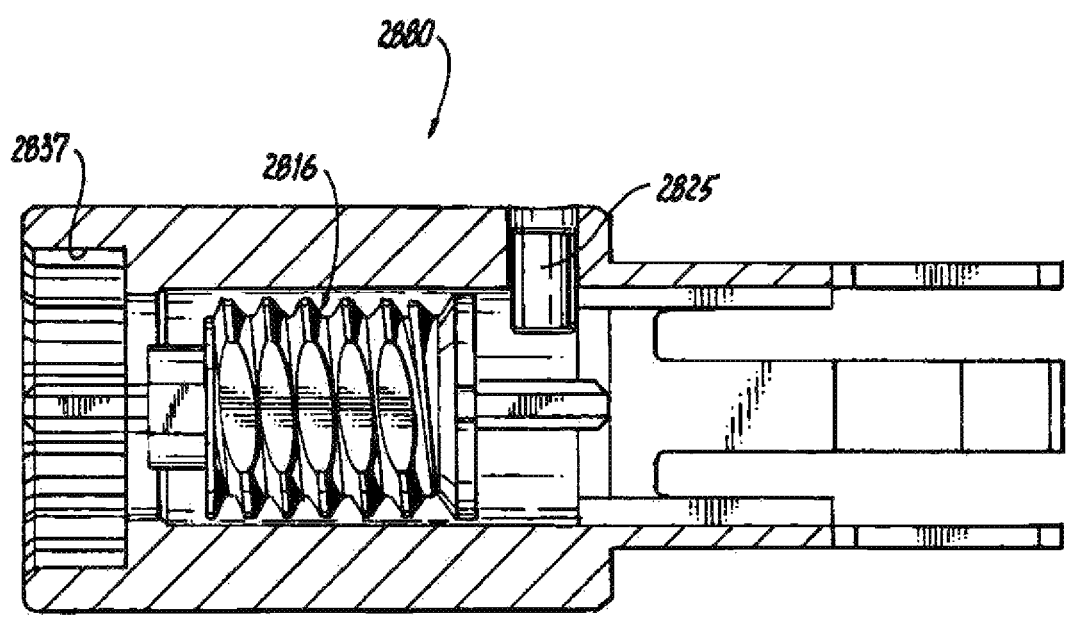
FIG. 28 is a cross-sectional view of an insertion adaptor that is configured to integrally carry the removable body portion of the implant body.
Figure 29:
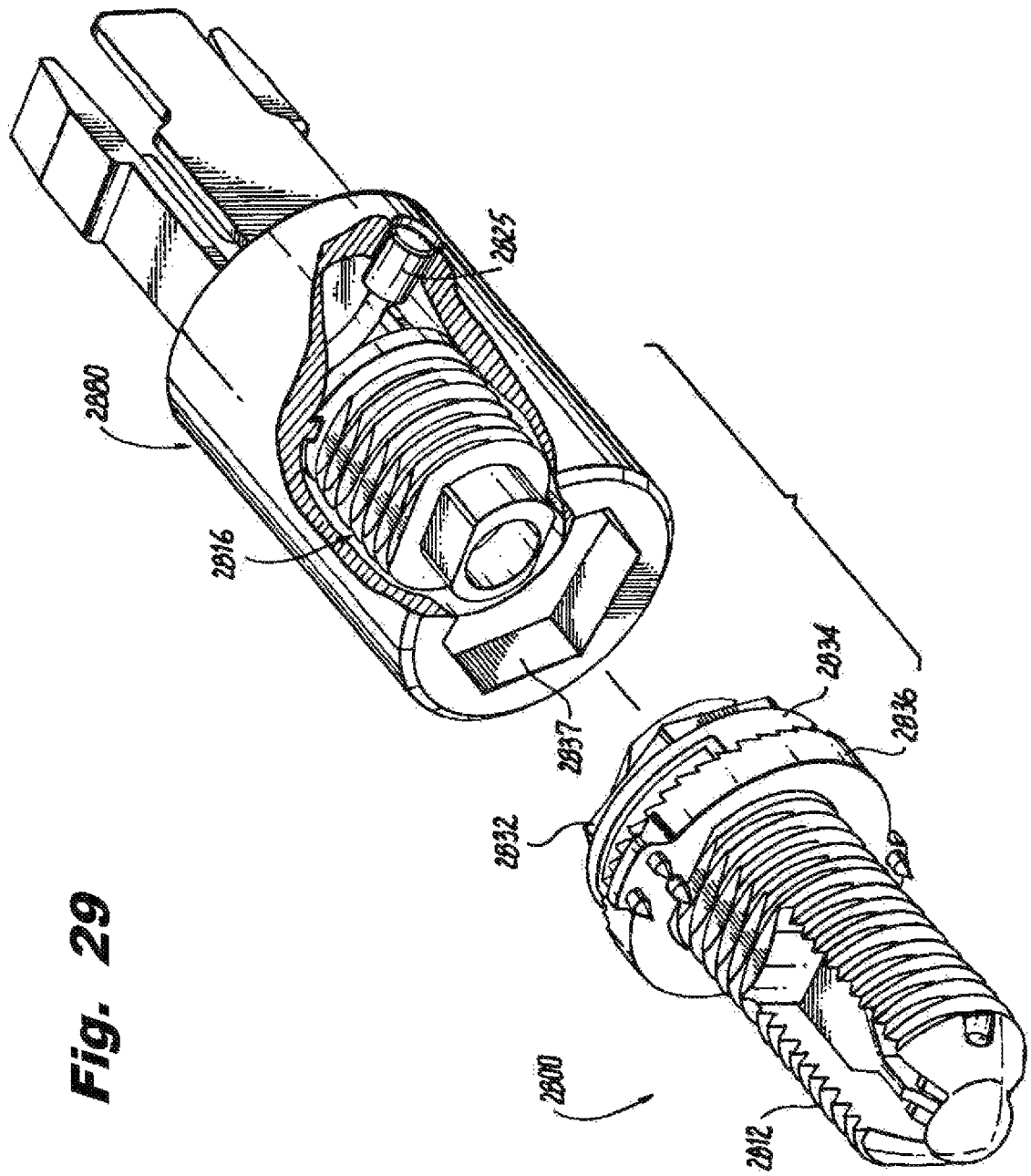
FIG. 29 is a perspective view of the insertion adapter shown in FIG. 28 prior to being mechanical connected to the proximal end of the main body portion of the implant of the subject invention.

Referring now to FIG. 28, there is illustrated an insertion adaptor 2880 that is configured to integrally carry a removable body portion 2816 of the interspinous implant 2800 shown in FIG. 29. That is, the removable body portion 2816 is carried in the adapter 2880 which is configured to be attached to the distal end of an insertion/removal tool not shown, prior to being mechanical connected to the proximal end of the main body portion 2812 of the implant 2800 by way of a mechanical connection, such as for example, the anti-rotation interference fit connection that is shown in FIGS. 22 and 23.

Figure 30:
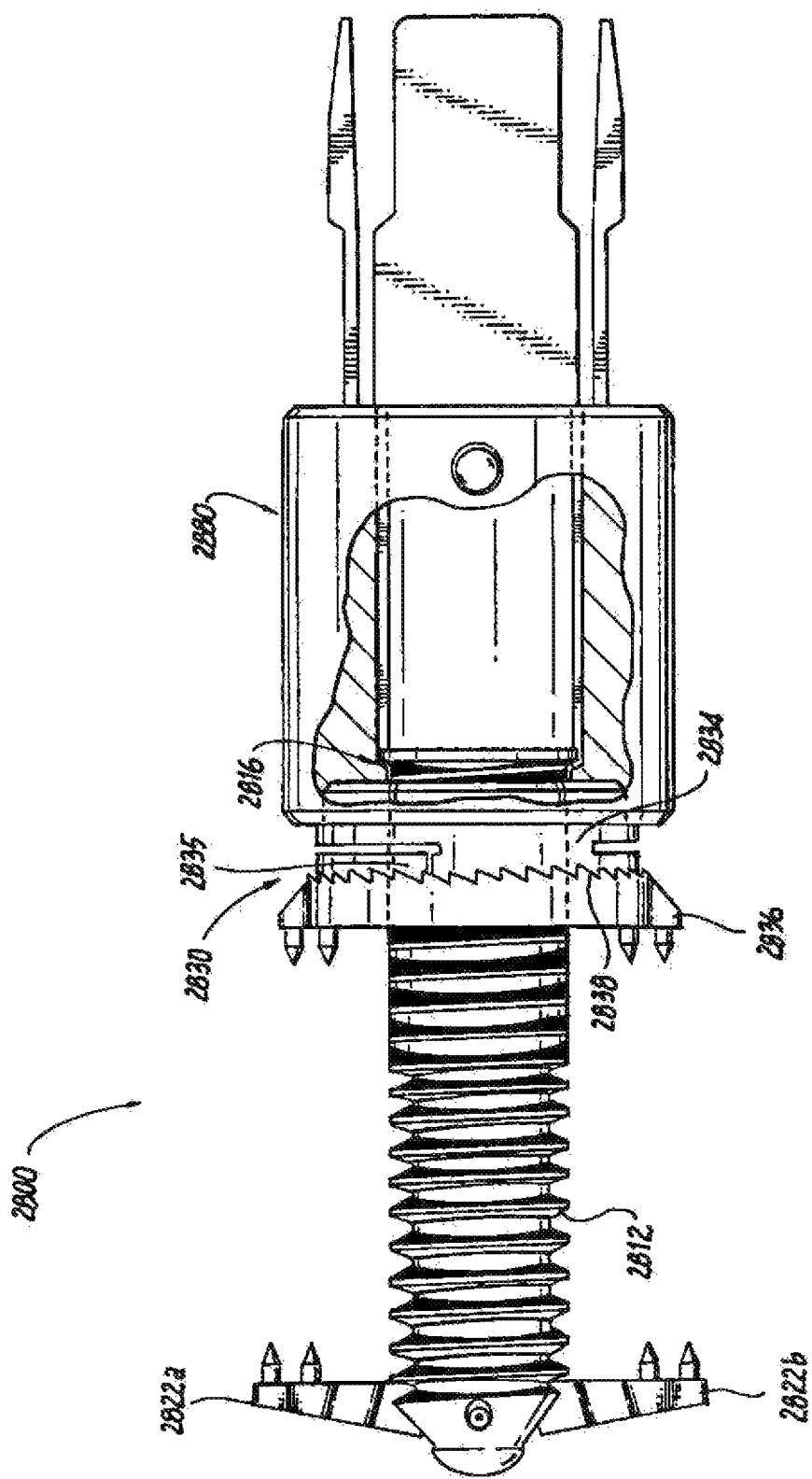
FIG. 30 is a side elevational view showing the main body portion of the implant connected to the removable body portion of the implant located with the adapter, prior to approximation of the distal anchor assembly and the proximal anchor assembly.
Figure 31:
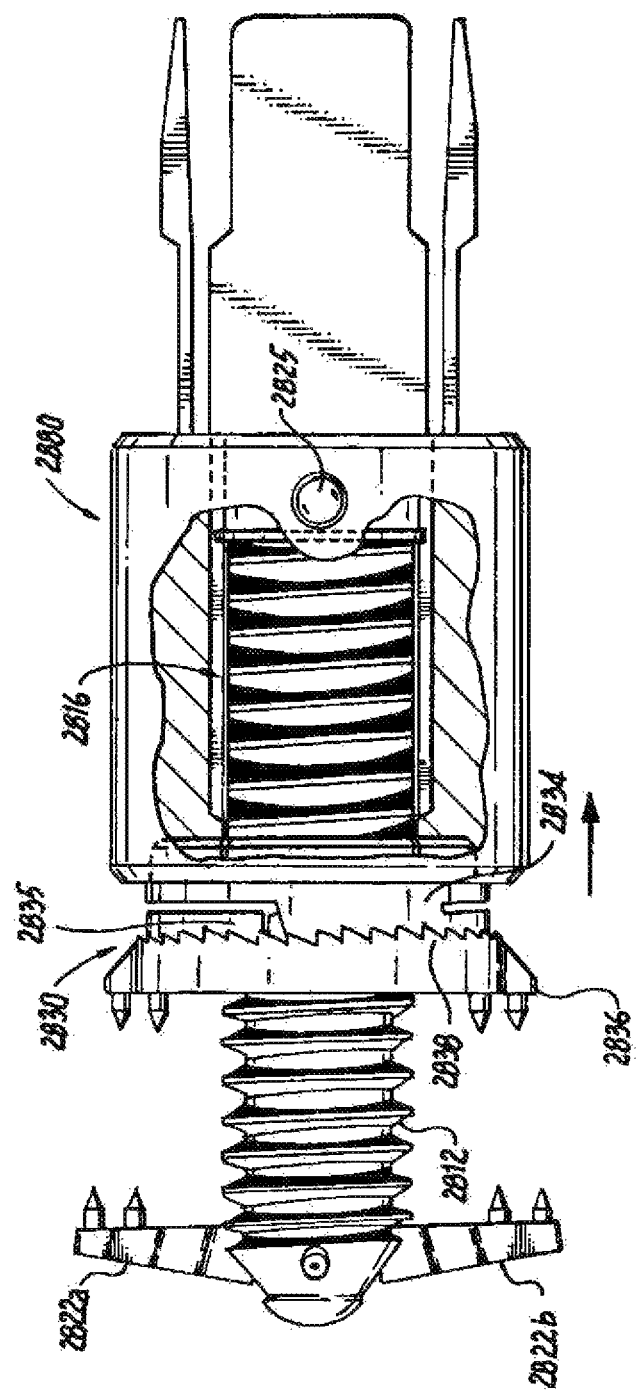
FIG. 31 is a side elevational view as in FIG. 20, after the proximal anchor assembly and distal anchor assembly have been approximated, and before the removable body portion with the adapter has been disconnected from the main body portion.

Referring to FIG. 30, to connect the two parts of the implant body 2800 together, the removable body portion 2816 is moved to a distal-most position inside the adapter 2880 using an insertion tool. Thereupon, the proximal end of the main body portion 2812 is joined with the removable body portion 2816 and the threaded locking ring 2834 of the proximal anchor assembly 2830 is positioned to provide added compression to maintain the tight fit between the two structures. At such a time, the hexagonal head 2832 of the locking ring 2834 of anchor assembly 2830 is received within the hexagonal distal recess 2837 of the adaptor 2880. As the proximal anchor assembly 2830 is approximated toward the distal anchor blades 2822a, 2822b, by rotation of the adapter 2880, the removable body portion 2816 travels proximally within the bore of the adapter 2880, limited in the extent of its movement by retaining pin 2825, as shown in FIG. 31.

Figure 32:
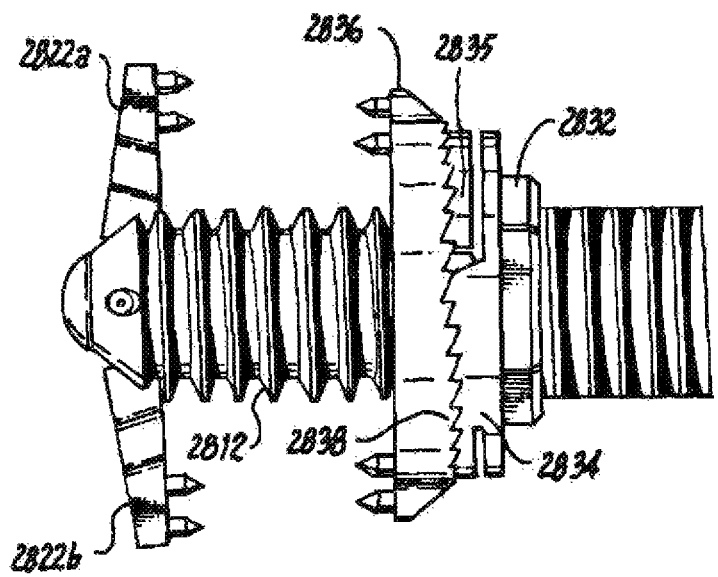
FIG. 32 is a side elevational view of the implant illustrated in FIGS. 29-31, after the removable body portion has been disconnected from the main body portion.

Continued rotation of the adapter 2880 causes the locking ring 2834 of the proximal anchor assembly 2830 to positively engage the anchor collar 2836. More particularly, the distal facing teeth on the cantilevered annular pawl members 2835 of locking ring 2834 positively engage the toothed rack 2838 on the proximal surface of the anchor collar 2836 to secure the position of the proximal anchor assembly 2830. At such a time, the adapter 2880 can be retracted, carrying with it the removable body portion 2816, thereby advantageously reducing the length of the implant, to the benefit of the patient, as shown in FIG. 32.

Figure 33:
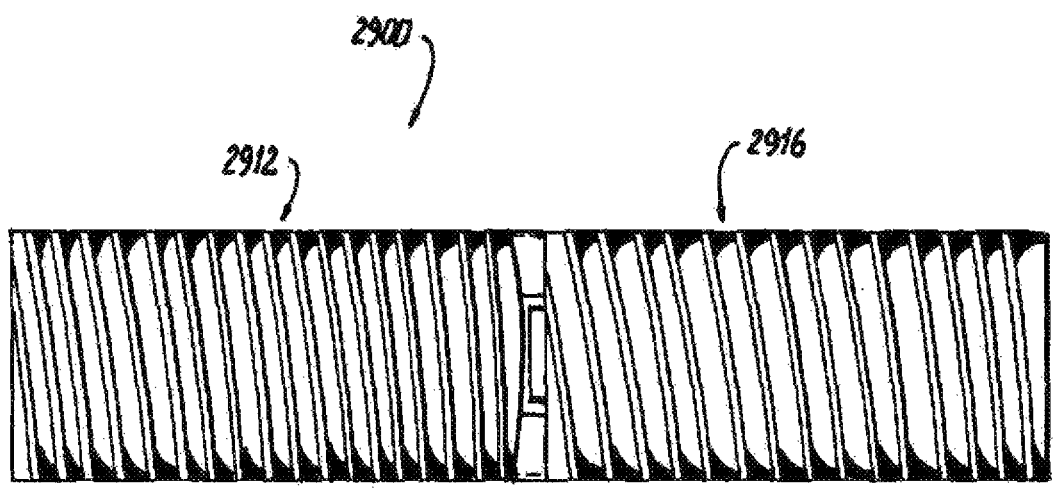
FIG. 33 is a side elevational view of yet another embodiment of the implant body of the subject invention, wherein the main body portion and the removable body portion are connected to one another by a threaded connection and a ratchet connection.
Figure 34:
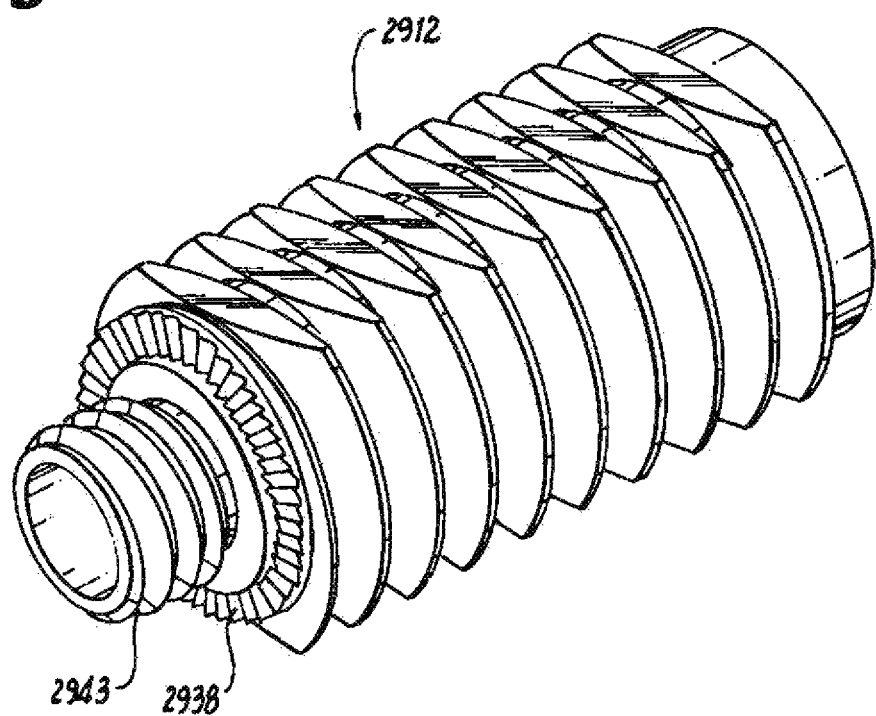
FIG. 34 is a perspective view of the removable end portion of the implant body as shown in FIG. 33, wherein the distal end of the removable body portion includes an annular rack of teeth disposed around a threaded distal stem.
Figure 35:
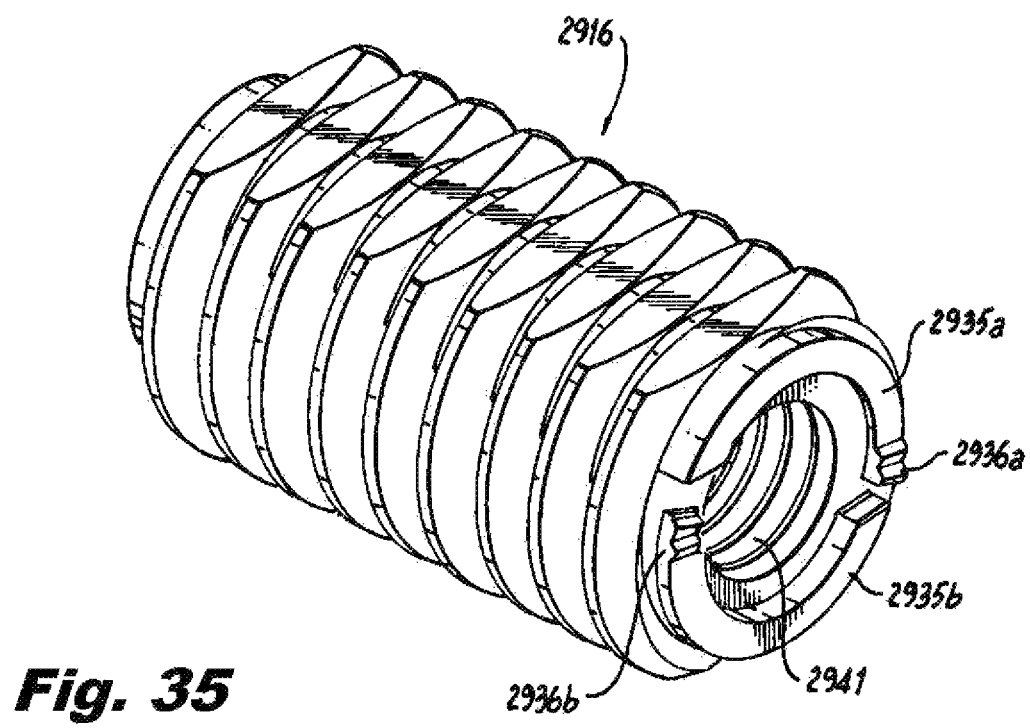
FIG. 35 is a perspective view of the main body portion wherein the proximal end thereof includes a pair of diametrically opposed arcuate pawl members disposed about a threaded proximal bore for engaging the annular rack on the removable body portion shown in FIG. 34.

In yet another embodiment of the subject invention shown in FIGS. 33-35, the implant body 2900 includes main body portion 2912 and a removable body portion 2916 which are operatively and releasably connected to one another by way of a ratchet connection. More particularly, as shown in FIG. 34, the main body portion 2912 includes a toothed rack 2938 disposed around a cannulated threaded distal stem 2943. As shown in FIG. 35, the removable body portion 2916 includes a pair of diametrically opposed, arcuate shaped, cantilevered pawls 2935a, 2935b, each with proximally facing teeth 2936a, 2936b. The pawls 2935a, 2935b are disposed about a threaded bore 2941 and are configured for selective (and reversible) engagement with the toothed rack 2938, upon rotation of the removable body portion 2916 relative to the main body portion 2912 of the implant body 2900. It is envisioned that the ratchet connection and the threaded connection associated with the two body portions of implant body 2900 could be transposed. Moreover, the combined threaded and ratcheted connection can be readily and reversibly disconnected once the implant body 2900 has been positioned in the interspinous processes space, to advantageously reduce the overall length thereof.

Figure 36:
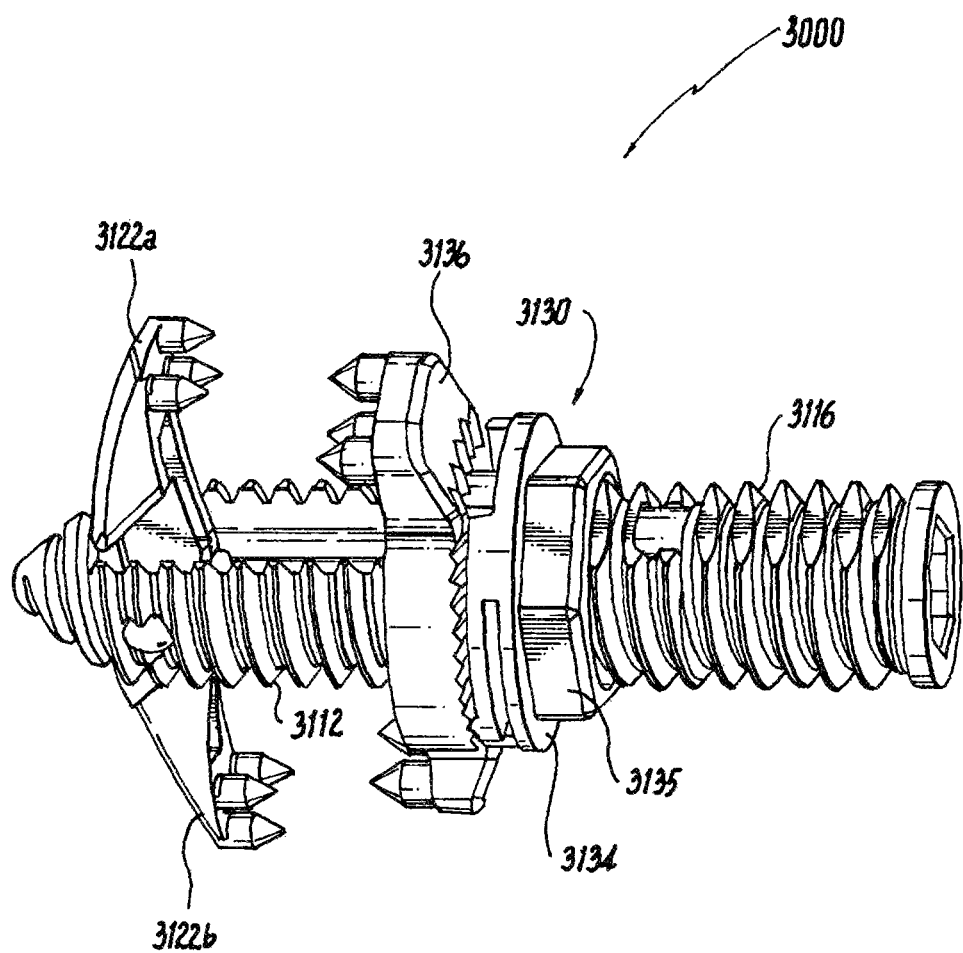
FIG. 36 is a perspective view of another interspinous process implant constructed in accordance with an embodiment of the subject invention, which includes a main body portion and a removable body portion.

Referring now to FIG. 36, there is illustrated another interspinous process implant constructed in accordance with a preferred embodiment of the subject invention, which is designated generally by reference numeral 3000 and includes a main body portion 3112 and a removable body portion 3116 that are detachable connected to one another.

Figure 37:
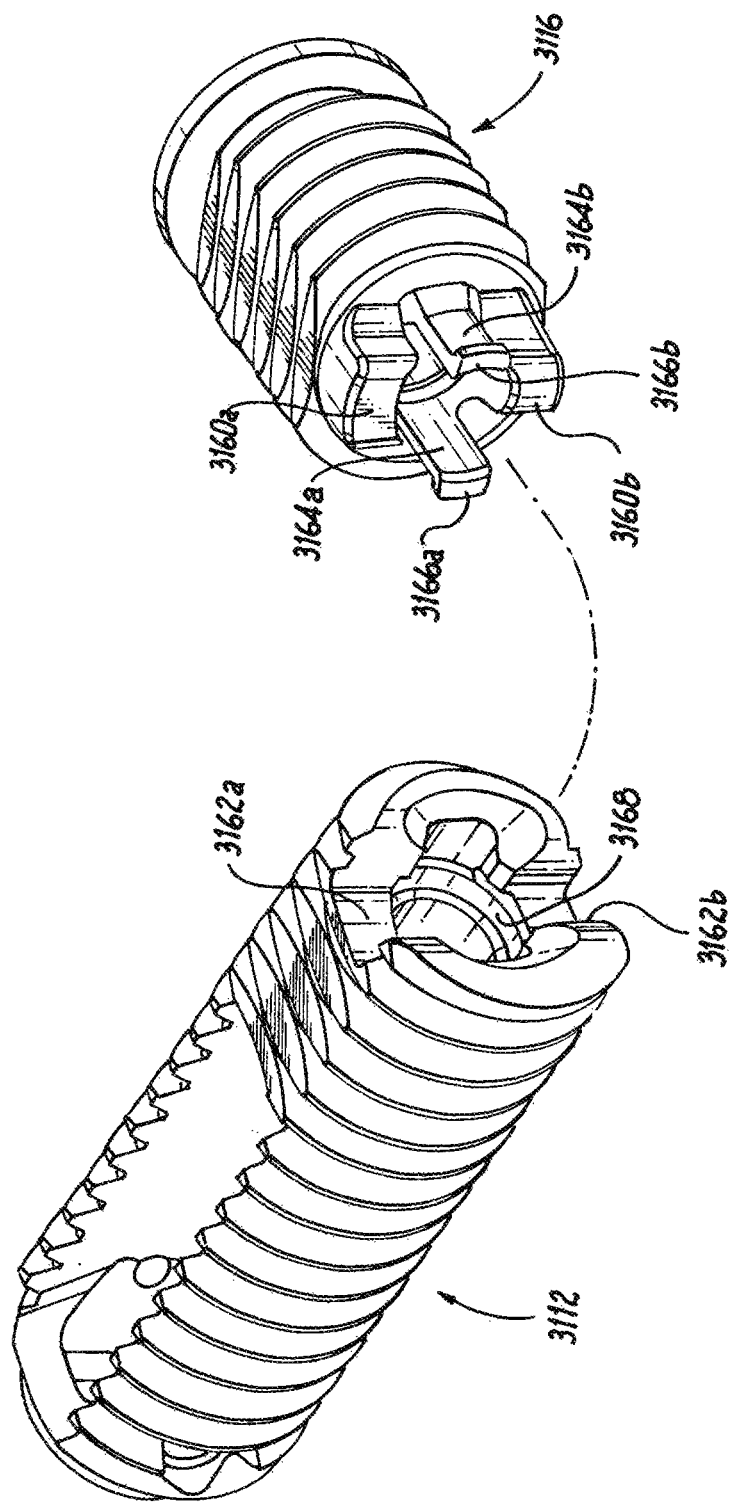
FIG. 37 is a perspective view of the implant body of the implant shown in FIG. 36, wherein the removable body portion includes diametrically opposed arcuate torque tabs that are sized to prevent the incorrect assembly of the main body portion and the removable body portion, and wherein the retention features for the implant body are diametrically opposed cantilevered dynamic members which interface with corresponding features in the main body portion.

As best seen in FIG. 37, the removable body portion 3116 includes a pair of diametrically opposed, distally extending arcuate torque tabs 3160a and 3160b that are dimensioned and configured to engage complementary arcuate slots 3162a and 3162b in the proximal end of the main body portion 3112. Moreover, torque tab 3160a and slot 3162a are sized differently from torque tab 3160b and slot 3162b to prevent misalignment of the main body portion 3112 and the removable body portion 3116 during assembly. This will ensure that the thread running along the implant body remains properly timed and aligned. The removable body portion 3116 further includes cooperating retention features in the form of diametrically opposed cantilevered dynamic tabs 3164a and 3164b, with respective radially out-turned feet 3166a and 3166b, for interfacing with an annular channel 3138 formed in the wall of the central bore 3142 of the main body portion 3112.

Figure 38:
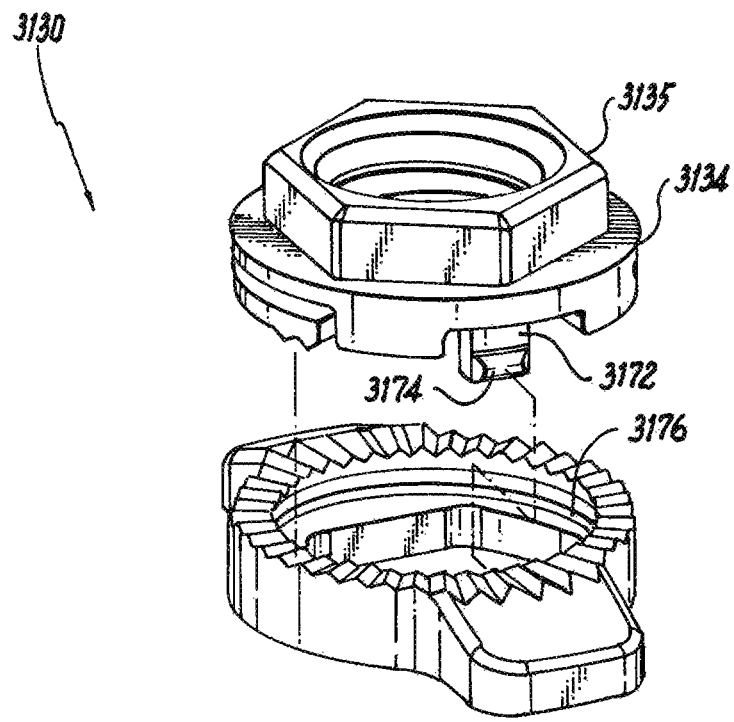
FIG. 38 is a perspective view of the proximal anchor assembly of the implant shown in FIG. 36, with the two parts separated for ease of illustration, wherein the threaded nut includes axial tabs with radially outwardly extending feet configured to engage an annular groove in the anchor plate to allow relative rotation of the two parts, while keeping them attached.
Figure 39:
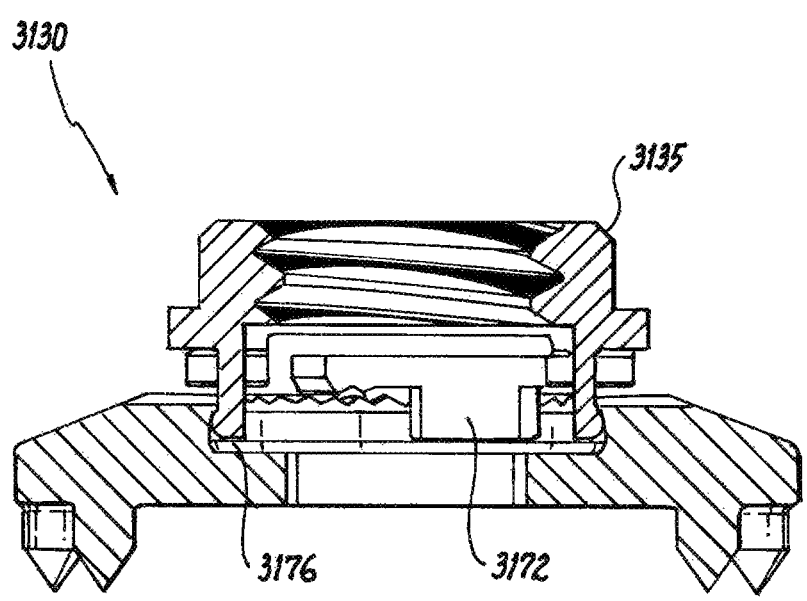
FIG. 39 is a cross-sectional view of the proximal anchor assembly shown in FIG. 38, in an assembled condition, with the axial tabs of the nut engaged in the annular groove of the anchor plate.

Referring now to FIG. 38, the proximal anchor assembly 3130 of implant 3000 includes a threaded locking nut 3134 having a hexagonal proximal head portion 3135 and distally extending deflectable tabs 3172 having radially outwardly extending feet 3174 that are dimensioned and configured to cooperatively engage an annular groove 3176 in the interior bore of anchor plate 3136. This will allow relative rotation of the two parts of anchor assembly 3130, while keeping them attached to one another, as shown in FIG. 39.

Figure 40:
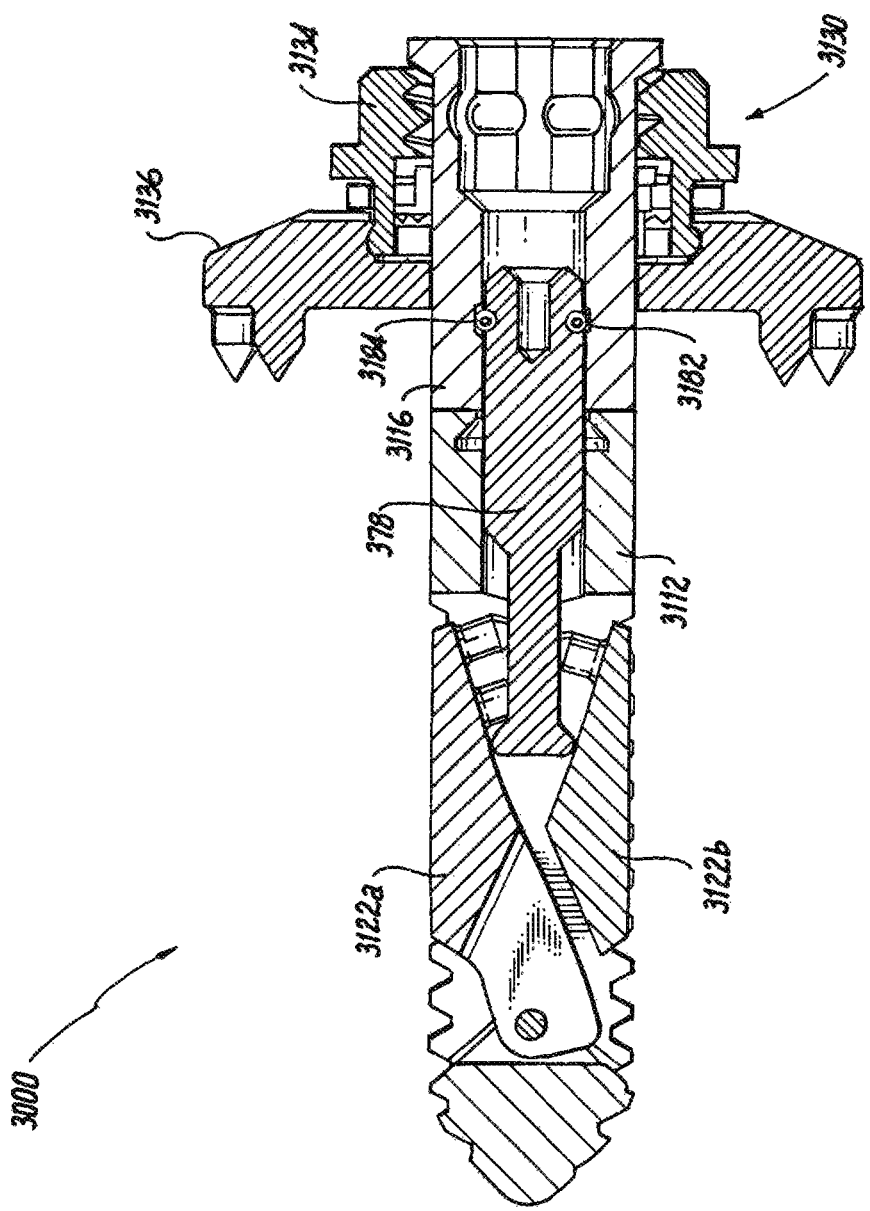
FIG. 40 is a cross-sectional view of the implant of FIG. 36, with the anchor blades of the distal anchor assembly shown in a stowed position within main body portion and with the proximal anchor assembly shown in an unapproximated position on the removable body portion, and wherein the internal plunger is retained in its proximal position by an annular spring detent feature.
Figure 41:
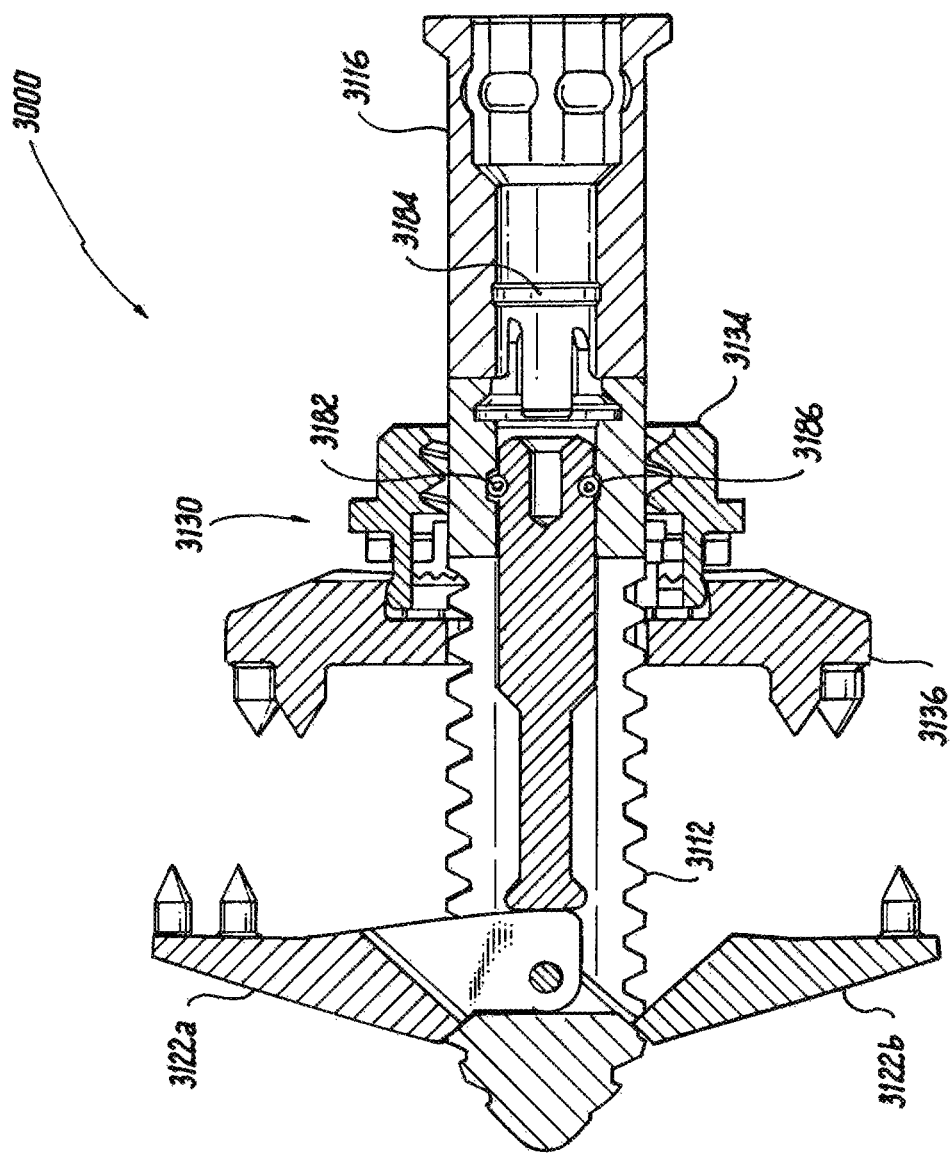
FIG. 41 is a cross-sectional view of the implant of FIG. 36, with the anchor blades of the distal anchor assembly shown in a radially deployed position stowed position and with the proximal anchor assembly shown in an approximated position on the main body portion, and wherein the internal plunger is in a distally advanced position retained by the annular spring detent feature.

Referring to FIG. 40, wherein with the distal anchor blades 3122a and 3122b are shown in a stowed position within the interior cavity of the main body portion 3112 of implant 3000 and the proximal anchor assembly 3130 is shown in an unapproximated position on the removable body portion 3116 of implant 3000. There is further shown in FIG. 40 the internal plunger 3180 retained in its proximal position by an annular retention spring 3182 seated within an annular groove 3184 in the bore of the removable body portion 3116. When the plunger 3180 is advanced distally to radially deploy the distal anchor blades 3122a and 3122b, the internal plunger 3180 becomes retained in its distal position by the annular retention spring 3182 seating within an annular groove 3184 in the bore of the main body portion 3112, as shown in FIG. 41.

While the apparatuses and methods of subject invention have been shown and described with reference to preferred embodiments, it is to be understood that any feature described in connection with one embodiment can be advantageously applied to other embodiments of the invention, even if not explicitly described in connection therewith, if such feature(s) are not mutually exclusive with other features of such embodiment. Nevertheless, those skilled in the art will readily appreciate that further changes or modifications may be made to devices and methods of the present invention without departing from the spirit and scope thereof.

What is claimed is:

1. An interspinous process implant comprising:
   a) an elongated threaded implant body defining a longitudinal axis and having a main body portion with opposed proximal and distal end portions, and a removable body portion operatively connected to the proximal end portion of the main body portion, wherein the elongated implant body is threaded along the length thereof, including the main body portion and the removable body portion;
   b) a distal anchor assembly including two deployable anchor blades mounted for pivotal movement between a stowed position located within an interior cavity of the main body portion and a deployed position radially extending from the main body portion; and
   c) a proximal anchor assembly including an anchor collar mounted for longitudinal movement along the longitudinal axis of the implant body between a first position spaced apart from the distal anchor assembly and a second position approximated with the distal anchor assembly.

2. An interspinous process implant as recited in claim 1, further comprising a locking ring threadably associated with the implant body for securing the axial position of the anchor collar with respect to the implant body.

3. An interspinous process implant as recited in claim 2, wherein the locking ring has a pair of diametrically opposed, arcuate shaped, cantilevered pawls, each with distal facing teeth for engaging a corresponding set of teeth on a proximal facing surface of the anchor collar.

4. An interspinous process implant as recited in claim 2, wherein the anchor collar and the locking ring of the proximal anchor assembly are operatively connected to one another to in such a manner so as to allow relative rotation of the anchor collar and locking ring.

5. An interspinous process implant as recited in claim 1, wherein the main body portion and the removable body portion are connected to one another by way of a threaded connection.

6. An interspinous process implant as recited in claim 1, wherein the main body portion has threaded proximal bore and the removable body portion has a threaded distal shaft section for threadably engaging the threaded proximal bore of the main body portion.

7. An interspinous process implant as recited in claim 1, wherein the main body portion and the removable body portion are connected to one another by way of a frangible connection.

8. An interspinous process implant as recited in claim 1, wherein the main body portion and the removable body portion are connected to one another by way of an interference fit.

9. An interspinous process implant as recited in claim 8, wherein the main body portion has a proximal tapered bore and the removable body portion has a frusto-conical distal end section for frictionally engaging the tapered bore of the main body portion.

10. An interspinous process implant as recited in claim 8, wherein the main body portion has an annual reception slot formed in a proximal end thereof and the removable body portion has an annular flange extending from the distal end thereof for frictionally engaging the annular reception slot of the main body portion.

11. An interspinous process implant as recited in claim 8, wherein the main body portion has proximal bore with diametrically opposed flattened anti-rotation walls and the removable body portion has a distal stem with corresponding diametrically opposed flattened anti-rotation surfaces.

12. An interspinous process implant as recited in claim 1, wherein the main body portion and the removable body portion are connected to one another by way of an a plurality of circumferentially spaced apart interlocking structures.

13. An interspinous process implant as recited in claim 12, wherein the main body portion includes a proximal bore including a set of circumferentially spaced apart radially inwardly projecting hemi-spherical protuberances for engaging a corresponding set of circumferentially spaced apart radially inwardly extending hemi-spherical recess formed on a distal stem of the removable body portion.

14. An interspinous process implant as recited in claim 12, wherein the main body portion includes a bore including a set of circumferentially spaced apart radially outwardly projecting hemi-spherical recesses for engaging a corresponding set of circumferentially spaced apart radially outwardly extending hemi-spherical protuberances formed on a distal stem of the removable body portion.

15. An interspinous process implant as recited in claim 14, wherein the proximal bore in the main body portion has a polygonal cross-section and the distal stem of the removable body portion has a corresponding polygonal cross-section.

16. An interspinous process implant as recited in claim 15, wherein the hemi-spherical protuberances on the distal stem of the removable body portion are spring loaded.

17. An interspinous process implant as recited in claim 15, wherein each of the hemi-spherical protuberances on the distal stem of the removable body portion are located on an integrally formed flexible cantilevered tab.

18. An interspinous process implant as recited in claim 1, wherein the main body portion and the removable body portion are connected to one another by way of a ratchet connection.

19. An interspinous process implant as recited in claim 18, wherein the main body portion includes a pair of diametrically opposed, arcuate shaped, cantilevered pawls, each with proximally facing teeth for engaging a corresponding set of teeth on a distal facing surface of the removable body portion.

20. An interspinous process implant as recited in claim 1, wherein the removable body portion is made of a biological material that can be absorbed over time by a patient's body.

21. An interspinous process implant as recited in claim 1, wherein the removable body portion includes a proximal bore for receiving a distal end portion of a removal tool.

22. An interspinous process implant as recited in claim 1, wherein an actuation assembly is disposed within the implant body for selectively deploying the distal anchor assembly, and wherein the actuation assembly includes a plunger body mounted for longitudinal movement between a proximal position and a distal position.

23. An interspinous process implant as recited in claim 22, wherein the plunger body includes a proximal annular spring for releasably engaging an annular groove formed within an interior cavity of the removable body portion and a distal annular spring for releasably engaging an annular groove formed within the interior cavity of the main body portion, to mechanically connect the releasable body portion to the main body portion.

24. An interspinous process implant as recited in claim 23, wherein movement of the plunger body from its proximal position to its distal position, to deploy the distal anchor assembly, further results in disconnecting the removable body portion from the main body portion.

25. An interspinous process implant as recited in claim 22, where the actuation assembly prevents separation of the main body portion and the removable body portion when disposed in a first position, and allows separation of the main body portion and the removable body portion when disposed in a second position.

26. An interspinous process implant as recited in claim 1, wherein the main body portion and the removable body portion are operatively connected to one another by way of an insertion instrument that spans a common interior bore extending at least partially through the implant body.

27. An interspinous process implant as recited in claim 1, wherein the removable body portion is carried within a tool adapter.

28. An interspinous process implant as recited in claim 1, wherein the removable body portion includes a pair of distally extending arcuate torque transmitting tabs for engaging interlocking arcuate channels formed in a proximal end of the main body portion for transmitting applied forces from the removable body portion to the main body portion.

29. An interspinous process implant as recited in claim 28, where the interlocking arcuate torque transmitting tabs and arcuate channels are dimensioned and configured such that the main body portion and the removable body portion are only engaged in one orientation, enabling threads on the exterior of the main body portion and the removable body portion to be timed such that the proximal anchor assembly can threadably transition between the body portions.

30. An interspinous process implant as recited in claim 1, wherein the threaded implant body is profiled such that the threading does not impede a rotationally engaged member to longitudinally move from the removable body portion to main body portion, if mis-alignment exists between the two body portions.

31. A method of implanting an interspinous process implant comprising the steps of:
   a) positioning an elongated implant body in a patient's body between two adjacent spinous processes, wherein the implant body includes a main body portion with opposed proximal and distal end portions, and a removable body portion operatively connected to the proximal end portion of the main body portion, wherein the main body portion and the removable body portion are threaded; and
   b) disconnecting the removable body portion of the implant body from the main body portion of the implant body; and
   c) removing the removable body portion from the patient's body.

32. A method of implanting an interspinous process implant according to claim 31, further comprising the step of deploying a distal anchor assembly from a stowed position located within an interior cavity of the main body portion.

33. A method of implanting an interspinous process implant according to claim 31, further comprising the step of moving a proximal anchor assembly along a longitudinal axis of the implant body between a first position associated with the removable body portion and spaced apart from the distal anchor assembly and a second position associated with the main body portion and approximated with the distal anchor assembly.

* * * * *